United States Patent [19]

O'Brien

[11] Patent Number: 5,700,909
[45] Date of Patent: Dec. 23, 1997

[54] PROSAPOSIN AND CYTOKINE-DERIVED PEPTIDES

[75] Inventor: John S. O'Brien, San Diego, Calif.

[73] Assignee: The Regents of the University of California, Oakland, Calif.

[21] Appl. No.: 232,513

[22] Filed: Apr. 21, 1994

Related U.S. Application Data

[63] Continuation-in-part of Ser. No. 100,247, Jul. 30, 1993, Pat. No. 5,571,787.

[51] Int. Cl.$^6$ .................................................. C07K 14/52
[52] U.S. Cl. ........................................... 530/326; 530/327
[58] Field of Search ........................... 530/300, 350, 530/326, 327, 351; 514/2, 12

[56] References Cited

FOREIGN PATENT DOCUMENTS 9311238  6/1993  WIPO .

OTHER PUBLICATIONS

Aderka, et al., "IL-6 Inhibits Lipopolysaccharide-Induced Tumor Necrosis Factor Production . . . ", *Journ. of Immun.*, 143:11:3517-3523, Dec. 19989.

Banks, et al., "Permeability of the Blood-Brain Barrier to Peptides: An Approach . . . ", *Peptides*, 13:1289-1294 (1992).

Barde, "Trophic Factors and Neuronal Survival", *Neuron*, 1:1525-1534, Jun. 1989.

Bazan, "Neuropoietic Cytokines In the Hematopoietic Fold", *Neuron*, 7:197-208, Aug. 1991.

Dewji, et al., "Nucleotide Sequence of Cloned cDNA For Human Sphingolipid Activator . . . ", *Proc. Natl. Acad. Sci. USA*, 84:8652-8656, Dec. 1987.

Fonnum, "A Rapid Radiochemical Method For the Determination of Choline Acetyltransferase", *Journ. of Neurochemistry*, 24:407-409 (1975).

Hefti, et al., "Function of Neurotrophic Factors In the Adult and Aging Brain . . . ", *Neurobiology of Aging*, 10:515-533 (1989).

Henderson, et al., "Neurotrophic Factors In Development and Plasticity of Spinal Neurons", *Restorative Neurology and Neuroscience*, 5:15-28 (1993).

Hiraiwa, et al., "Binding and Transport of Gangliosides By Prosaposin", *Proc. Natl. Acad. Sci. USA*, 89:11254-11258, Dec. 1992.

Hiraiwa, et al., "Isolation, Characterization, and Proteolysis of Human Prosaposin . . . ", *Archives of Biochemistry and Biophysics*, 304:1:110-116 1933.

Hofer, et al., "Brain-Derived Neurotrophic Factor Prevents Neuronal Death In Vivo", *Nature*, 331:261-262, Jan. 1988.

Ip, et al., "The Neurotrophins and CNTF: Specificity of Action Toward PNS and CNS Neurons" *J. Physiol.*, 85:123-130 (1991).

Kishimoto, et al., "Saposins: Structure, Function, Distribution, and Molecular Genetics", *Journal of Lipid Research*, 3:1255-1268 (1992).

Krystal, "A Simple Microassay For Erythropoietin Based On $^3$H-Thymidine Incorporation . . . ", *Exp. Hermatol.*, 11:7:649-660, Aug. 1983.

Lin, et al., "Purification, Cloning, and Expression of Ciliary Neurotrophic Factor (CNTF)", *Science*, 246:1023-1025, Nov. 1989.

Lindsay, et al., "The Neurotrophin Family of NGF-Related Neurotrophic Factors", *Restorative Neurology and Neuroscience*, 2:211-220 (1991).

Maisonpierre, et al., "Neurotrophin-3: A Neurotrophic Factor Related to NGF and BDNF", *Science*, 247:1446-1451, Mar. 1990.

Morimoto, et al., "Distribution of Saposin Proteins (Sphingolipid . . . ", *Proc. Natl. Acad. Sci. USA*, 87:3493-3497, May 1990.

O'Brien, et al., "Saposin Proteins: Structure, Function, and Role in Human Lysosomal . . . ", *FASEB Journal*, 5:301-308, Mar. 1991.

O'Brien, et al., "Coding of Two Sphingolipid Activator Proteins (SAP-1 and SAP-2) . . . ", *Science*, 241:1098-1101, Aug. 1988.

Purves, et al., "Trophic Regulation of Nerve Cell Morphology and Innervation . . . ", *Nature*, 336:123-128, Nov. 1988.

Rich, et al., "Nerve Growth Factor Protects Adult Sensory Neurons From Cell Death . . . ", *Journal of Neurocytology*, 16:261-268 (1987).

Satomi, "Developmental Changes of Glutamate Decarboxylase and 2', 3'-Cyclic Nucleotide . . . ", *Zoological Science*, 9:127-132 (1992).

Sprang, et al., "Cytokine Structural Taxonomy and Mechanisms of Receptor Engagement", *Current Opinion in Structural Biology*, 3:815-827 (1993).

Triguero, et al., "Capillary Depletion Method For Quantification of Blood-Brain Barrier Transport of Circulating Peptides and Plasma Proteins", *J. of Neurochem.*, 54:6:1882-1888 (1990).

Baringe, M. (1994) Neurotrophic factors enter the clinic. Science 264:772-774.

Bradová, V. et al. (1993) Prosaposin deficiency: further characterization of the sphingolipid activator protein-deficient sibs. Human Genetics 92:143-152.

Dewji, N. et al. (1986) Molecular cloning of the sphingolipid activator protein . . . Biochemical and Biophysical Research Communications 134(2):989-994.

Francis, M. et al. (1990) Immunological properties of hepatitis B core antigen fusion proteins. Proc. Natl. Acad. Sci. 87:2545-2549.

(List continued on next page.)

Primary Examiner—Marianne P. Allen
Assistant Examiner—Robert C. Hayes
Attorney, Agent, or Firm—Fish & Richardson, P.C.

[57] ABSTRACT

Prosaposin and peptide derivatives derived therefrom will promote neurite outgrowth in vitro. A peptide consensus sequence was determined by comparing the active neurite outgrowth-inducing saposin C peptide sequence with that of various hematopoietic and neuropoietic cytokines. These cytokine-derived peptides will promote the same processes as their corresponding cytokines. In addition, prosaposin and saposin C promote increased nerve cell myelination ex vivo.

9 Claims, 7 Drawing Sheets

OTHER PUBLICATIONS

Fürst, W. et al. (1990) The complete amino–acid sequences of human ganglioside GM2 activator protein and cerebroside sulfate activator protein. Eur. J. Biochem. 192:709–714.

Kleinschmidt, T. et al. (1987) Complete amino–acid sequence and carbohydrate content of the naturally occurring glucosylceramide activator protein . . . Biological Chemistry Hoppe–Seyler 368(12):1573–1578.

Kondoh, K. et al. (1993) Distribution of prosaposin–like immunoreactivity in rat brain. The Journal of Comparative Neurology 334:590–602.

Kondoh, K. et al. (1991) Isolation and characterization of prosaposin from human milk. Biochemical and Biophysical Research Communication 181(1):286–292.

Lamontagne, S. et al. (1994) Modulation of human saposin B sphingolipid–binding specificity by alternative splicing. The Journal of Biological Chemistry 269:20528–20532.

Morimoto, S. et al. (1989) Saposin A: Second cerebrosidase activator protein. Proc. Natl. Acad. Sci. 86:3389–3393.

Morimoto, S. et al. (1988) Saposin D: A sphingomyelinase activator. Biochemical and Biophysical Research Communications 156(1):403–410.

O'Brien, J. et al. (1994) Identification of prosaposin as a neurotrophic factor. Proc. Natl. Acad. Sci. 91(20):9593–9596.

O'Brien, J. et al. (1992) Isolation and characterization of prosaposin . . . FASEBJ. 6(4):A969.

Priestle, J.P. et al. (1989) Crystallographic refinement of interleukin . . . Proc. Natl. Acad. Sci. 86:9667–9671.

Rorman, E. et al. (1992) Structure and evolution of the human prosaposin chromosomal gene. Genomics 12(2):312–318.

Sano, A. et al. (1991) Saposin–C from bovine spleen: complete amino acid sequence and relation between the structure and its biological activity. Biochimica Acta 1120(1):75–80.

Soeda, S. et al. (1993) Binding of cerebrosides and sulfatides to saposins A–D*. The Journal of Biological Chemistry 268(25):18519–18523.

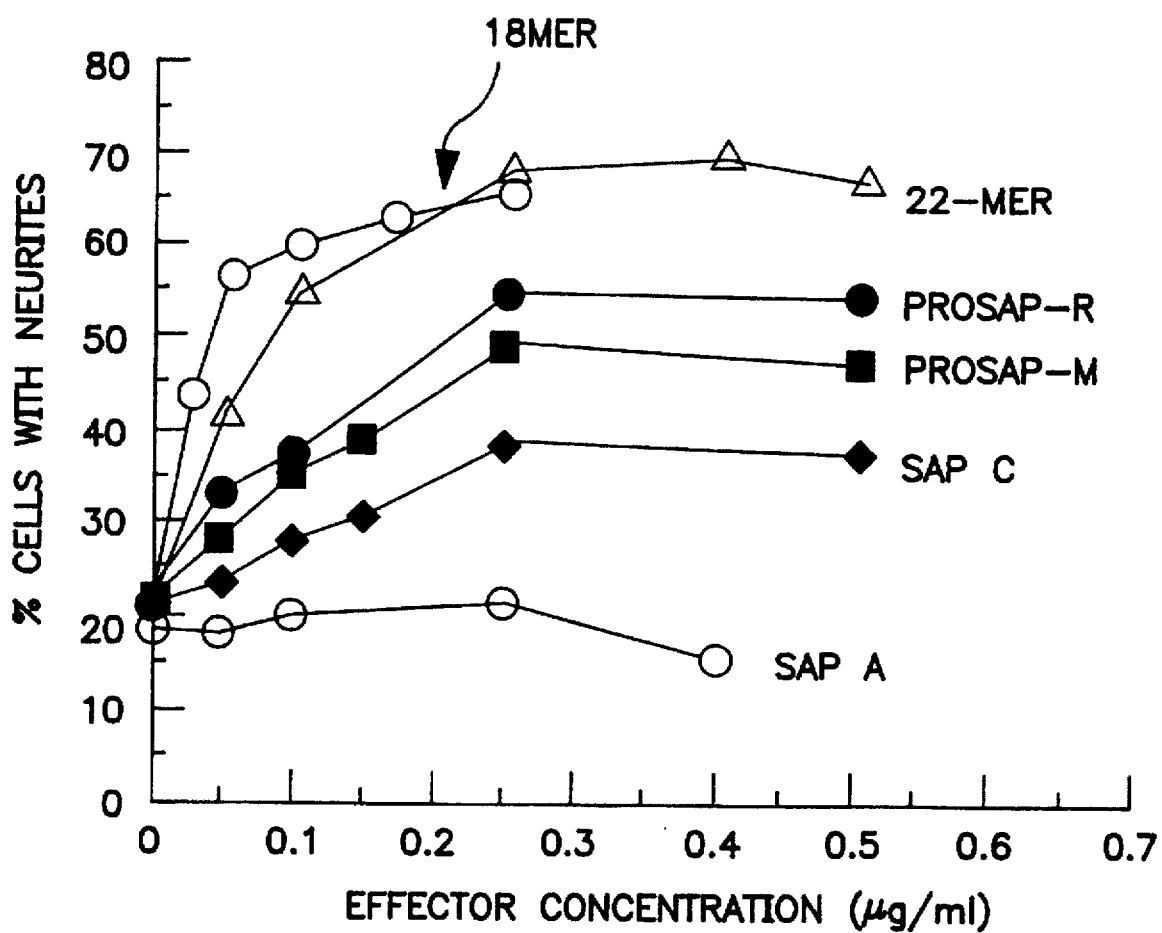
FIG. IA

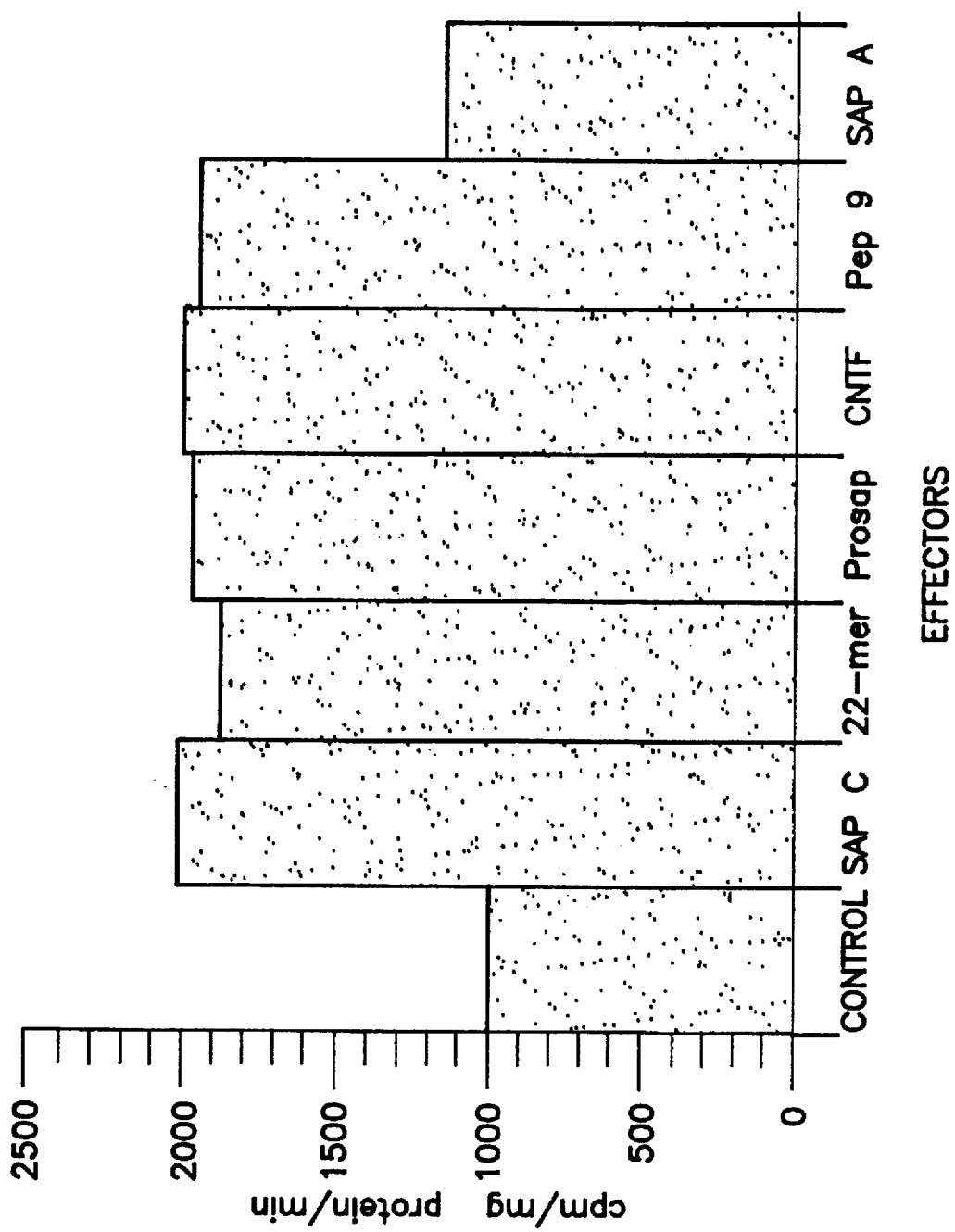

```
                        8                   18                  29
HUMAN  (1)*    C E F L V K E V T K L I D N N K T E K E I L
MOUSE  (15)    C Q F V M N K F S E L I V N N A T E E L L Y
RAT    (16)    C Q L V N R K L S E L I I N N A T E E L L •
G. PIG (17)    C E Y V V K K V M L L I D N N R T E E K I I
BOVINE (18)    C E F V V K E V A K L I D N N R T E E E I L

CONSENSUS      C • • • V • • • • L I • N N • T E • • I •
(19)                                                   (L)

7                   17                  28
SAPOSIN A      C K D V V T A A G D M L K D N A T E E E I L
(20)
```

*NUMBERS IN PARENTHESES ( ) INDICATE SEQ. ID NO.

FIG. 3B

SEQUENCE LISTING ( 1 ) GENERAL INFORMATION:

( i i i ) NUMBER OF SEQUENCES: 20

( 2 ) INFORMATION FOR SEQ ID NO:1:

( i ) SEQUENCE CHARACTERISTICS:
        ( A ) LENGTH: 22 amino acids
        ( B ) TYPE: amino acid
        ( D ) TOPOLOGY: linear ( i i ) MOLECULE TYPE: peptide ( i x ) FEATURE:
        ( A ) NAME/KEY: Peptide
        ( B ) LOCATION: 1..22
        ( D ) OTHER INFORMATION: /label=SapC ( x i ) SEQUENCE DESCRIPTION: SEQ ID NO:1:

```
Cys Glu Phe Leu Val Lys Glu Val Thr Lys Leu Ile Asp Asn Asn Lys
 1               5                  10                  15
Thr Glu Lys Glu Ile Leu
               20
```

( 2 ) INFORMATION FOR SEQ ID NO:2:

( i ) SEQUENCE CHARACTERISTICS:
        ( A ) LENGTH: 20 amino acids
        ( B ) TYPE: amino acid
        ( D ) TOPOLOGY: linear ( i i ) MOLECULE TYPE: peptide ( i x ) FEATURE:
        ( A ) NAME/KEY: Peptide
        ( B ) LOCATION: 1..20
        ( D ) OTHER INFORMATION: /label=hCNTF ( x i ) SEQUENCE DESCRIPTION: SEQ ID NO:2:

```
Tyr Val Lys His Gln Gly Leu Asn Lys Asn Ile Asn Leu Asp Ser Val
 1               5                  10                  15
Asp Gly Val Pro
               20
```

( 2 ) INFORMATION FOR SEQ ID NO:3:

( i ) SEQUENCE CHARACTERISTICS:
        ( A ) LENGTH: 523 amino acids
        ( B ) TYPE: amino acid
        ( D ) TOPOLOGY: linear ( i i ) MOLECULE TYPE: protein ( i x ) FEATURE:
        ( A ) NAME/KEY: Protein
        ( B ) LOCATION: 1..523
        ( D ) OTHER INFORMATION: /label=Hum_prosaposin ( x i ) SEQUENCE DESCRIPTION: SEQ ID NO:3:

```
Met Tyr Ala Leu Phe Leu Leu Ala Ser Leu Leu Gly Ala Ala Leu Ala
 1               5                  10                  15
```

```
Gly Pro Val Leu Gly Leu Lys Glu Cys Thr Arg Gly Ser Ala Val Trp
            20              25              30
Cys Gln Asn Val Lys Thr Ala Ser Asp Cys Gly Ala Val Lys His Cys
        35              40              45
Leu Gln Thr Val Trp Asn Lys Pro Thr Val Lys Ser Leu Pro Cys Asp
    50              55              60
Ile Cys Lys Asp Val Val Thr Ala Ala Gly Asp Met Leu Lys Asp Asn
65              70              75              80
Ala Thr Glu Glu Glu Ile Leu Val Tyr Leu Gly Lys Thr Cys Asp Trp
            85              90              95
Leu Pro Lys Pro Asn Met Ser Ala Ser Cys Lys Glu Ile Val Asp Ser
            100             105             110
Tyr Leu Pro Val Ile Leu Asp Ile Ile Lys Gly Glu Met Ser Arg Pro
            115             120             125
Gly Glu Val Cys Ser Ala Leu Asn Leu Cys Glu Ser Leu Gln Lys His
        130             135             140
Leu Ala Glu Leu Asn His Gln Lys Gln Leu Glu Ser Asn Lys Ile Pro
145             150             155             160
Glu Leu Asp Met Thr Glu Val Val Ala Pro Phe Met Ala Asn Ile Pro
                165             170             175
Leu Leu Leu Tyr Pro Gln Asp Gly Pro Arg Ser Lys Pro Gln Pro Lys
            180             185             190
Asp Gly Asp Val Cys Gln Asp Cys Ile Gln Met Val Thr Asp Ile Gln
        195             200             205
Thr Ala Val Arg Thr Asn Ser Thr Phe Val Gln Ala Leu Val Glu His
    210             215             220
Val Lys Glu Glu Cys Asp Arg Leu Gly Pro Gly Met Ala Asp Ile Cys
225             230             235             240
Lys Asn Tyr Ile Ser Gln Tyr Ser Glu Ile Ala Ile Gln Met Met Met
                245             250             255
His Met Gln Pro Lys Glu Ile Cys Ala Leu Val Gly Phe Cys Asp Glu
            260             265             270
Val Lys Glu Met Pro Met Gln Thr Leu Val Pro Ala Lys Val Ala Ser
            275             280             285
Lys Asn Val Ile Pro Ala Leu Asp Leu Val Asp Pro Ile Lys Lys His
        290             295             300
Glu Val Pro Ala Lys Ser Asp Val Tyr Cys Glu Val Cys Glu Phe Leu
305             310             315             320
Val Lys Glu Val Thr Lys Leu Ile Asp Asn Asn Lys Thr Glu Lys Glu
                325             330             335
Ile Leu Asp Ala Phe Asp Lys Met Cys Ser Lys Leu Pro Lys Ser Leu
            340             345             350
Ser Glu Glu Cys Gln Glu Val Val Asp Thr Tyr Gly Ser Ser Ile Leu
        355             360             365
Ser Ile Leu Leu Glu Glu Val Ser Pro Glu Leu Val Cys Ser Met Leu
    370             375             380
His Leu Cys Ser Gly Thr Arg Leu Pro Ala Leu Thr Val His Val Thr
385             390             395             400
Gln Pro Lys Asp Gly Phe Cys Glu Val Cys Lys Lys Leu Val Gly
            405             410             415
Tyr Leu Asp Arg Asn Leu Glu Lys Asn Ser Thr Lys Gln Glu Ile Leu
            420             425             430
Ala Ala Leu Glu Lys Gly Cys Ser Phe Leu Pro Asp Pro Tyr Gln Lys
```

|   | 435 | | | | 440 | | | | 445 | | | |
|---|---|---|---|---|---|---|---|---|---|---|---|---|
| Gln | Cys | Asp | Gln | Phe | Val | Ala | Glu | Tyr | Glu | Pro | Val | Leu | Ile | Glu | Ile |
|     | 450 |     |     |     |     | 455 |     |     |     |     | 460 |     |     |     |     |
| Leu | Val | Glu | Val | Met | Asp | Pro | Ser | Phe | Val | Cys | Leu | Lys | Ile | Gly | Ala |
| 465 |     |     |     |     | 470 |     |     |     |     | 475 |     |     |     |     | 480 |
| Cys | Pro | Ser | Ala | His | Lys | Pro | Leu | Leu | Gly | Thr | Glu | Lys | Cys | Ile | Trp |
|     |     |     |     | 485 |     |     |     |     | 490 |     |     |     |     | 495 |     |
| Gly | Pro | Ser | Tyr | Trp | Cys | Gln | Asn | Thr | Glu | Thr | Ala | Ala | Gln | Cys | Asn |
|     |     |     | 500 |     |     |     |     | 505 |     |     |     |     | 510 |     |     |
| Ala | Val | Glu | His | Cys | Lys | Arg | His | Val | Trp | Asn |
|     |     |     | 515 |     |     |     | 520 |     |     |     |

( 2 ) INFORMATION FOR SEQ ID NO:4:

( i ) SEQUENCE CHARACTERISTICS:
        ( A ) LENGTH: 80 amino acids
        ( B ) TYPE: amino acid
        ( D ) TOPOLOGY: linear ( i i ) MOLECULE TYPE: peptide ( i x ) FEATURE:
        ( A ) NAME/KEY: Peptide
        ( B ) LOCATION: 1..80
        ( D ) OTHER INFORMATION: /label=Saposin_C ( x i ) SEQUENCE DESCRIPTION: SEQ ID NO:4:

| Ser | Asp | Val | Tyr | Cys | Glu | Val | Cys | Glu | Phe | Leu | Val | Lys | Glu | Val | Thr |
|---|---|---|---|---|---|---|---|---|---|---|---|---|---|---|---|
| 1   |     |     |     | 5   |     |     |     |     | 10  |     |     |     |     | 15  |     |
| Lys | Leu | Ile | Asp | Asn | Asn | Lys | Thr | Glu | Lys | Glu | Ile | Leu | Asp | Ala | Phe |
|     |     |     | 20  |     |     |     |     | 25  |     |     |     |     | 30  |     |     |
| Asp | Lys | Met | Cys | Ser | Lys | Leu | Pro | Lys | Ser | Leu | Ser | Glu | Glu | Cys | Gln |
|     |     | 35  |     |     |     |     | 40  |     |     |     |     | 45  |     |     |     |
| Glu | Val | Val | Asp | Thr | Tyr | Gly | Ser | Ser | Ile | Leu | Ser | Ile | Leu | Leu | Glu |
|     | 50  |     |     |     |     | 55  |     |     |     |     | 60  |     |     |     |     |
| Glu | Val | Ser | Pro | Glu | Leu | Val | Cys | Ser | Met | Leu | His | Leu | Cys | Ser | Gly |
| 65  |     |     |     |     | 70  |     |     |     |     | 75  |     |     |     |     | 80  |

( 2 ) INFORMATION FOR SEQ ID NO:5:

( i ) SEQUENCE CHARACTERISTICS:
        ( A ) LENGTH: 2740 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: misc_feature
        ( B ) LOCATION: 1..2740
        ( D ) OTHER INFORMATION: /label=Hum_prosaposin ( x i ) SEQUENCE DESCRIPTION: SEQ ID NO:5:

```
ATGTACGCCC TCTTCCTCCT GGCCAGCCTC CTGGGCGCGG CTCTAGCCGG CCCGGTCCTT      60

GGACTGAAAG AATGCACCAG GGGCTCGGCA GTGTGGTGCC AGAATGTGAA GACGGCGTCC     120

GACTGCGGGG CAGTGAAGCA CTGCCTGCAG ACCGTTTGGA ACAAGCCAAC AGTGAAATCC     180

CTTCCCTGCG ACATATGCAA AGACGTTGTC ACCGCAGCTG GTGATATGCT GAAGGACAAT     240

GCCACTGAGG AGGAGATCCT TGTTTACTTG GAGAAGACCT GTGACTGGCT TCCGAAACCG     300

AACATGTCTG CTTCATGCAA GGAGATAGTG GACTCCTACC TCCCTGTCAT CCTGGACATC     360

ATTAAAGGAG AAATGAGCCG TCCTGGGGAG GTGTGCTCTG CTCTCAACCT CTGCGAGTCT     420
```

| | | | | | |
|---|---|---|---|---|---|
| CTCCAGAAGC | ACCTAGCAGA | GCTGAATCAC | CAGAAGCAGC | TGGAGTCCAA | TAAGATCCCA | 480
| GAGCTGGACA | TGACTGAGGT | GGTGGCCCCC | TTCATGGCCA | ACATCCCTCT | CCTCCTCTAC | 540
| CCTCAGGACG | GCCCCCGCAG | CAAGCCCCAG | CCAAAGGATA | ATGGGGACGT | TTGCCAGGAC | 600
| TGCATTCAGA | TGGTGACTGA | CATCCAGACT | GCTGTACGGA | CCAACTCCAC | CTTTGTCCAG | 660
| GCCTTGGTGG | AACATGTCAA | GGAGGAGTGT | GACCGCCTGG | GCCTGGCAT | GGCCGACATA | 720
| TGCAAGAACT | ATATCAGCCA | GTATTCTGAA | ATTGCTATCC | AGATGATGAT | GCACATGCAA | 780
| CCCAAGGAGA | TCTGTGCGCT | GGTTGGGTTC | TGTGATGAGG | TGAAAGAGAT | GCCCATGCAG | 840
| ACTCTGGTCC | CCGCCAAAGT | GGCCTCCAAG | AATGTCATCC | CTGCCCTGGA | ACTGGTGGAG | 900
| CCCATTAAGA | AGCACGAGGT | CCCAGCAAAG | TCTGATGTTT | ACTGTGAGGT | GTGTGAATTC | 960
| CTGGTGAAGG | AGGTGACCAA | GCTGATTGAC | AACAACAAGA | CTGAGAAAGA | AATACTCGAC | 1020
| GCTTTTGACA | AAATGTGCTC | GAAGCTGCCG | AAGTCCCTGT | CGGAAGAGTG | CCAGGAGGTG | 1080
| GTGGACACGT | ACGGCAGCTC | CATCCTGTCC | ATCCTGCTGG | AGGAGGTCAG | CCCTGAGCTG | 1140
| GTGTGCAGCA | TGCTGCACCT | CTGCTCTGGC | ACGCGGCTGC | CTGCACTGAC | CGTTCACGTG | 1200
| ACTCAGCCAA | AGGACGGTGG | CTTCTGCGAA | GTGTGCAAGA | AGCTGGTGGG | TTATTTGGAT | 1260
| CGCAACCTGG | AGAAAAACAG | CACCAAGCAG | GAGATCCTGG | CTGCTCTTGA | GAAAGGCTGC | 1320
| AGCTTCCTGC | CAGACCCTTA | CCAGAAGCAG | TGTGATCAGT | TTGTGGCAGA | GTACGAGCCC | 1380
| GTGCTGATCG | AGATCCTGGT | GGAGGTGATG | GATCCTTCCT | TCGTGTGCTT | GAAAATTGGA | 1440
| GCCTGCCCCT | CGGCCCATAA | GCCCTTGTTG | GGAACTGAGA | AGTGTATATG | GGGCCCAAGC | 1500
| TACTGGTGCC | AGAACACAGA | GACAGCAGCC | CAGTGCAATG | CTGTCGAGCA | TTGCAAACGC | 1560
| CATGTGTGGA | ACTAGGAGGA | GGAATATTCC | ATCTTGGCAG | AAACCACAGC | ATTGGTTTTT | 1620
| TTCTACTTGT | GTGTCTGGGG | GAATGAACGC | ACAGATCTGT | TTGACTTTGT | TATAAAAATA | 1680
| GGGCTCCCCC | ACCTCCCCCA | TTTCTGTGTC | CTTTATTGTA | GCATTGCTGT | CTGCAAGGGA | 1740
| GCCCCTAGCC | CCTGGCAGAC | ATAGCTGCTT | CAGTGCCCCT | TTTCTCTCTG | CTAGATGGAT | 1800
| GTTGATGCAC | TGGAGGTCTT | TTAGCCTGCC | CTTGCATGGC | GCCTGCTGGA | GGAGGAGAGA | 1860
| GCTCTGCTGG | CATGAGCCAC | AGTTTCTTGA | CTGGAGGCCA | TCAACCCTCT | TGGTTGAGGC | 1920
| CTTGTTCTGA | GCCCTGACAT | GTGCTTGGGC | ACTGGTGGGC | CTGGGCTTCT | GAGGTGGCCT | 1980
| CCTGCCCTGA | TCAGGGACCC | TCCCCGCTTT | CCTGGGCCTC | TCAGTTGAAC | AAAGCAGCAA | 2040
| AACAAAGGCA | GTTTTATATG | AAAGATTAGA | AGCCTGGAAT | AATCAGGCTT | TTAAATGAT | 2100
| GTAATTCCCA | CTGTAATAGC | ATAGGGATTT | GGAAGCAGC | TGCTGGTGGC | TTGGGACATC | 2160
| AGTGGGGCCA | AGGGTTCTCT | GTCCCTGGTT | CAACTGTGAT | TTGGCTTTCC | CGTGTCTTTC | 2220
| CTGGTGATGC | CTTGTTTGGG | GTTCTGTGGG | TTTGGGTGGG | AAGAGGGCAA | TCTGCCTGAA | 2280
| TGTAACCTGC | TAGCTCTCCG | AAGGCCCTGC | GGGCCTGGCT | TGTGTGAGCG | TGTGGACAGT | 2340
| GGTGGCCGCG | CTGTGCCTGC | TCGTGTTGCC | TACATGTCCC | TGGCTGTTGA | GGCGCTGCTT | 2400
| CAGCCTGCAC | CCCTCCCTTG | TCTCATAGAT | GCTCCTTTTG | ACCTTTTCAA | ATAAATATGG | 2460
| ATGGCGAGCT | CCTAGGCCTC | TGGCTTCCTG | GTAGAGGGCG | GCATGCCGAA | GGGTCTGCTT | 2520
| GGTGTGGATT | GGATGCTGGG | GTGTGGGGGT | TGGAAGCTGT | CTGTGGCCCA | CTTGGGCACC | 2580
| CACGCTTCTG | TCCACTTCTG | GTTGCCAGGA | GACAGCAAGC | AAAGCCAGCA | GGACATGAAG | 2640
| TTGCTATTAA | ATGGACTTCG | TGATTTTTGT | TTTGCACTAA | AGTTTCTGTG | ATTTAACAAT | 2700
| AAAATTCTGT | TAGCCAGAAA | AAAAAAAAA | AAAAAAAAA | | | 2740

( 2 ) INFORMATION FOR SEQ ID NO:6:

( i ) SEQUENCE CHARACTERISTICS:
        ( A ) LENGTH: 18 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:6:

```
Tyr Lys Glu Val Thr Lys Leu Ile Asp Asn Asn Lys Thr Glu Lys Glu
1               5                   10                  15

Ile Leu
```

( 2 ) INFORMATION FOR SEQ ID NO:7:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( i x ) FEATURE:
        ( A ) NAME/KEY: Peptide
        ( B ) LOCATION: 1..15
        ( D ) OTHER INFORMATION: /label=hIL-6

( x i ) SEQUENCE DESCRIPTION: SEQ ID NO:7:

```
Glu Ala Leu Ala Glu Asn Asn Leu Asn Leu Pro Lys Met Ala Gly
1               5                   10                  15
```

( 2 ) INFORMATION FOR SEQ ID NO:8:

( i ) SEQUENCE CHARACTERISTICS:
        ( A ) LENGTH: 17 amino acids
        ( B ) TYPE: amino acid
        ( D ) TOPOLOGY: linear ( i i ) MOLECULE TYPE: peptide ( i x ) FEATURE:
        ( A ) NAME/KEY: Peptide
        ( B ) LOCATION: 1..17
        ( D ) OTHER INFORMATION: /label=hIL-2

( x i ) SEQUENCE DESCRIPTION: SEQ ID NO:8:

```
Leu Gln Met Ile Leu Asn Gly Ile Asn Asn Tyr Lys Asn Pro Lys Leu
1               5                   10                  15

Thr
```

( 2 ) INFORMATION FOR SEQ ID NO:9:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: peptide ( i x ) FEATURE:
        ( A ) NAME/KEY: Peptide
        ( B ) LOCATION: 1..12
        ( D ) OTHER INFORMATION: /label=hIL-3

( x i ) SEQUENCE DESCRIPTION: SEQ ID NO:9:

```
Ile Leu Met Glu Asn Asn Leu Arg Arg Pro Asn Leu
1               5                   10
```

( 2 ) INFORMATION FOR SEQ ID NO:10:

( i ) SEQUENCE CHARACTERISTICS:
( A ) LENGTH: 13 amino acids
( B ) TYPE: amino acid
( D ) TOPOLOGY: linear ( i i ) MOLECULE TYPE: peptide ( i x ) FEATURE:
( A ) NAME/KEY: Peptide
( B ) LOCATION: 1..13
( D ) OTHER INFORMATION: /label=hIL-gamma ( x i ) SEQUENCE DESCRIPTION: SEQ ID NO:10:

```
Phe Tyr Leu Arg Asn Asn Gln Leu Val Ala Gly Thr Leu
1               5                   10
```

( 2 ) INFORMATION FOR SEQ ID NO:11:

( i ) SEQUENCE CHARACTERISTICS:
( A ) LENGTH: 17 amino acids
( B ) TYPE: amino acid
( D ) TOPOLOGY: linear ( i i ) MOLECULE TYPE: peptide ( i x ) FEATURE:
( A ) NAME/KEY: Peptide
( B ) LOCATION: 1..17
( D ) OTHER INFORMATION: /label=hEPO ( x i ) SEQUENCE DESCRIPTION: SEQ ID NO:11:

```
Ala Glu His Cys Ser Leu Asn Glu Asn Ile Thr Val Pro Asp Thr Lys
1               5                   10                  15

Val
```

( 2 ) INFORMATION FOR SEQ ID NO:12:

( i ) SEQUENCE CHARACTERISTICS:
( A ) LENGTH: 18 amino acids
( B ) TYPE: amino acid
( D ) TOPOLOGY: linear ( i i ) MOLECULE TYPE: peptide ( i x ) FEATURE:
( A ) NAME/KEY: Peptide
( B ) LOCATION: 1..18
( D ) OTHER INFORMATION: /label=hLIF ( x i ) SEQUENCE DESCRIPTION: SEQ ID NO:12:

```
Tyr Thr Ala Gln Gly Glu Pro Phe Pro Asn Asn Val Glu Lys Leu Cys
1               5                   10                  15

Ala Pro
```

( 2 ) INFORMATION FOR SEQ ID NO:13:

( i ) SEQUENCE CHARACTERISTICS:
( A ) LENGTH: 15 amino acids
( B ) TYPE: amino acid
( D ) TOPOLOGY: linear ( i i ) MOLECULE TYPE: peptide ( i x ) FEATURE:
( A ) NAME/KEY: Peptide
( B ) LOCATION: 1..15
( D ) OTHER INFORMATION: /label=hIL-1beta ( x i ) SEQUENCE DESCRIPTION: SEQ ID NO:13:

```
Phe Asn Lys Ile Glu Ile Asn Asn Lys Leu Glu Phe Glu Ser Ala
```

(2) INFORMATION FOR SEQ ID NO:14:

(i) SEQUENCE CHARACTERISTICS:
        (A) LENGTH: 18 amino acids
        (B) TYPE: amino acid
        (D) TOPOLOGY: linear (ii) MOLECULE TYPE: peptide (ix) FEATURE:
        (A) NAME/KEY: Peptide
        (B) LOCATION: 1..18
        (D) OTHER INFORMATION: /label=hONC-M (xi) SEQUENCE DESCRIPTION: SEQ ID NO:14:

```
Arg Pro Asn Ile Leu Gly Leu Arg Asn Asn Ile Tyr Cys Met Ala Gln
 1               5                  10                  15
Leu Leu
```

(2) INFORMATION FOR SEQ ID NO:15:

(i) SEQUENCE CHARACTERISTICS:
        (A) LENGTH: 22 amino acids
        (B) TYPE: amino acid
        (D) TOPOLOGY: linear (ii) MOLECULE TYPE: peptide (ix) FEATURE:
        (A) NAME/KEY: Peptide
        (B) LOCATION: 1..22
        (D) OTHER INFORMATION: /label=Mouse (xi) SEQUENCE DESCRIPTION: SEQ ID NO:15:

```
Cys Gln Phe Val Met Asn Lys Phe Ser Glu Leu Ile Val Asn Asn Ala
 1               5                  10                  15
Thr Glu Glu Leu Leu Tyr
                20
```

(2) INFORMATION FOR SEQ ID NO:16:

(i) SEQUENCE CHARACTERISTICS:
        (A) LENGTH: 22 amino acids
        (B) TYPE: amino acid
        (D) TOPOLOGY: linear (ii) MOLECULE TYPE: peptide (ix) FEATURE:
        (A) NAME/KEY: Peptide
        (B) LOCATION: 22
        (D) OTHER INFORMATION: /note= "Xaa is a non-consensus residue"

(ix) FEATURE:
        (A) NAME/KEY: Peptide
        (B) LOCATION: 1..22
        (D) OTHER INFORMATION: /label=Rat (xi) SEQUENCE DESCRIPTION: SEQ ID NO:16:

```
Cys Gln Leu Val Asn Arg Lys Leu Ser Glu Leu Ile Ile Asn Asn Ala
 1               5                  10                  15
Thr Glu Glu Leu Leu Xaa
                20
```

(2) INFORMATION FOR SEQ ID NO:17:

(i) SEQUENCE CHARACTERISTICS:

(A) LENGTH: 22 amino acids
(B) TYPE: amino acid
(D) TOPOLOGY: linear (i i) MOLECULE TYPE: peptide (i x) FEATURE:
(A) NAME/KEY: Peptide
(B) LOCATION: 1..22
(D) OTHER INFORMATION: /label=G_Pig (x i) SEQUENCE DESCRIPTION: SEQ ID NO:17:

Cys Glu Tyr Val Val Lys Lys Val Met Leu Leu Ile Asp Asn Asn Arg
1               5                   10                  15

Thr Glu Glu Lys Ile Ile
            20

(2) INFORMATION FOR SEQ ID NO:18:

(i) SEQUENCE CHARACTERISTICS:
(A) LENGTH: 22 amino acids
(B) TYPE: amino acid
(D) TOPOLOGY: linear (i i) MOLECULE TYPE: peptide (i x) FEATURE:
(A) NAME/KEY: Peptide
(B) LOCATION: 1..22
(D) OTHER INFORMATION: /label=Bovine (x i) SEQUENCE DESCRIPTION: SEQ ID NO:18:

Cys Glu Phe Val Val Lys Glu Val Ala Lys Leu Ile Asp Asn Asn Arg
1               5                   10                  15

Thr Glu Glu Glu Ile Leu
            20

(2) INFORMATION FOR SEQ ID NO:19:

(i) SEQUENCE CHARACTERISTICS:
(A) LENGTH: 22 amino acids
(B) TYPE: amino acid
(D) TOPOLOGY: linear (i i) MOLECULE TYPE: peptide (i x) FEATURE:
(A) NAME/KEY: Peptide
(B) LOCATION: 2..4
(D) OTHER INFORMATION: /label=Consensus
    / note= "Xaa is a non-consensus residue."

(i x) FEATURE:
(A) NAME/KEY: Peptide
(B) LOCATION: 6..10
(D) OTHER INFORMATION: /note= "Xaa is a non-consensus residue."

(i x) FEATURE:
(A) NAME/KEY: Peptide
(B) LOCATION: 13
(D) OTHER INFORMATION: /note= "Xaa is a non-consensus residue"

(i x) FEATURE:
(A) NAME/KEY: Peptide
(B) LOCATION: 16
(D) OTHER INFORMATION: /note= "Xaa is a non-consensus residue."

(i x) FEATURE:
(A) NAME/KEY: Peptide
(B) LOCATION: 19..20
(D) OTHER INFORMATION: /note= "Xaa is a non-consensus residue."

(ix) FEATURE:
 (A) NAME/KEY: Peptide
 (B) LOCATION: 21
 (D) OTHER INFORMATION: /note= "Xaa is Ileucine or Leucine"

(ix) FEATURE:
 (A) NAME/KEY: Peptide
 (B) LOCATION: 22
 (D) OTHER INFORMATION: /note= "Xaa is a non-consensus residue."

(xi) SEQUENCE DESCRIPTION: SEQ ID NO:19:

```
Cys Xaa Xaa Xaa Val Xaa Xaa Xaa Xaa Leu Ile Xaa Asn Asn Xaa
 1               5                      10                  15

Thr Glu Xaa Xaa Xaa Xaa
            20
```

(2) INFORMATION FOR SEQ ID NO:20:

(i) SEQUENCE CHARACTERISTICS:
  (A) LENGTH: 22 amino acids
  (B) TYPE: amino acid
  (D) TOPOLOGY: linear (ii) MOLECULE TYPE: peptide (ix) FEATURE:
  (A) NAME/KEY: Peptide
  (B) LOCATION: 1..22
  (D) OTHER INFORMATION: /label=Saposin_A (xi) SEQUENCE DESCRIPTION: SEQ ID NO:20:

```
Cys Lys Asp Val Val Thr Ala Ala Gly Met Leu Lys Asp Asn Ala
 1               5                      10                  15

Thr Glu Glu Glu Ile Leu
            20
```

PROSAPOSIN AND CYTOKINE-DERIVED PEPTIDES

This application is a continuation-in part of U.S. Ser. No. 08/100,247, filed Jul. 30, 1993, now U.S. Pat. No. 5,571,787.

FIELD OF THE INVENTION

This invention discloses proteins and peptides having therapeutic properties. More specifically, these molecules are effective in promoting growth and differentiation of various cell types.

BACKGROUND OF THE INVENTION

Prosaposin, a 70 kilodalton glycoprotein, is the precursor of a group of four small heat-stable glycoproteins which are required for hydrolysis of glycosphingolipids by lysosomal hydrolases (Kishimoto et al., (1992) *J. Lipid Res.*, 33: 1255–1267) Prosaposin is proteolytically processed in lysosomes to generate saposins A, B, C, and D which exist as four adjacent tandem domains in prosaposin (O'Brien and Kishimoto, (1991) *FASEB J.*, 5: 301–308) All four saposins are structurally similar to each other, including the placement of six cysteines, a glycosylation site and conserved proline residues.

Unprocessed prosaposin also exists as an integral membrane protein and a secreted protein which is present in human milk, cerebrospinal fluid and seminal plasma. The presence of high concentrations of unprocessed prosaposin in the central nervous system indicates that it may play a significant role in addition to activation of lysosomal hydrolases.

Prosaposin binds membrane lipids called glycosphingolipids which are sphingolipids consisting of a carbohydrate head group and two hydrocarbon chains; a fatty acid and a sphingosine derivative. Glycosphingolipids are important components of the myelin sheath, a structure which protects and insulates nerve fibers. Demyelination is a defect common to a number of central nervous system disorders, the most common being multiple sclerosis (MS). MS, a chronic disorder which may lead to total disability, is characterized by damage to the myelin sheath leaving the axons mostly intact. It is currently believed that autoimmune mechanisms, perhaps vitally-induced, may play a role in development of the disease. There is currently no effective treatment for MS. Other central nervous system disorders involving demyelination include acute disseminated encephalomyelitis, amyotrophic lateral sclerosis, acute necrotizing hemorrhagic leukodystrophy, progressive multifocal leukoencephalitis, metachromatic leukodystrophy and adrenal leukodystrophy. An example of a demyelinating disease of the peripheral nervous system is Guillain-Barrésyndrome (*Pathologic Basis of Disease*, Robbins, S. L. and Cotran, R. S., eds, W. B. Saunders, Philadelphia, (1979), pp. 1578–1582).

Post-polio syndrome is characterized by muscle fatigue and decreased endurance with accompanying muscle weakness and atrophy. The disease is believed to be caused in part by the same type of spinal cord motor neuron damage as occurs in amyotrophic lateral sclerosis.

Peripheral nerve injuries and peripheral neuropathies, such as those resulting from diabetes or chemotherapy, comprise the most prevalent peripheral nervous system disorders (see Table 1) Current treatments for peripheral nerve disorders only treat the symptoms, not the cause of the disease.

TABLE 1

| Disease | No. of U.S. patients |
|---|---|
| Spinal Cord Injury | 500,000 |
| Macular Degeneration | 1,500,000 |
| Amyotrophic Lateral Sclerosis | 30,000 |
| Spinal Muscular Atrophy | 50,000 |
| Post-Polio Syndrome | 250,000 |
| Guillain-Barr''Syndrome | 20,000 |
| Muscular Dystrophies | 175,000 |
| Peripheral Neuropathies | 1,000,000 |
| Peripheral Nerve Injuries | 500,000 |
| Total | 4,150,000 |

Prosaposin binds glycosphingolipids such as gangliosides, cerebrosides and sulfatides with high affinity and facilitates their transfer from micelles to membranes (Sueda, et al. (1993) *J. Biol. Chem.* in press; Hiraiwa et al., (1992) *Proc. Natl. Acad. Sci. USA.*, 89: 11254–11258). Gangliosides contain one or more sialic acid residues and are most abundant in the plasma membrane of neurons where they constitute approximately 6% of the total lipid mass. Although the function of gangliosides is largely unknown, they have been implicated in the stimulation of neuronal differentiation, neuritogenesis and nervous system repair.

Neurotrophins may be defined as those proteins capable of affecting the survival, target innervation and/or function of neuronal cell populations (Barde, (1989) *Neuron*, 2: 1525–1534). The efficacy of neurotrophins both in vitro and in vivo has been well-documented. The most well-characterized of such proteins is nerve growth factor (NGF) which is synthesized by target cells of sympathetic and sensory neurons and acts as a trophic factor for forebrain cholinergic, peripheral and sensory neurons (Hefti et al., (1989) *Neurobiol. Aging*, 10: 515–533). In vivo experiments indicate that NGF can reverse naturally-occurring as well as physical traumatic injuries to peripheral nerves. For example, local application of NGF has been shown to prevent the atrophy of sensory ganglia resulting from transection of the sciatic nerve in adult rats (Rich et al., (1987) *J. Neurocytol.*, 16: 261–268). In addition, NGF plays a role in the neural regenerative process since it enhances neurite extension of developing sympathetic and sensory neurons (Purves et al., (1988) *Nature*, 336: 123–128). Moreover, since NGF supports the function of forebrain cholinergic neurons which are lost in Alzheimer's patients, this indicates that NGF may have a clinical use in treatment of this disease (Hefti et al., (1989) *Neurobiol. Aging*, 10: 515–533).

Brain-Derived Neurotrophic Factor (BDNF) is synthesized in the central nervous system and is a trophic factor for peripheral sensory neurons, dopaminergic neurons of the substantia nigra, central cholinergic neurons and retinal ganglia (Henderson et al., (1993) *Restor. Neurol. Neurosci.*, 5: 15–28). BDNF has also been shown to prevent normally-occurring cell death both in vitro and in vivo (Hofer and Barde, (1988) *Nature*, 331: 261–262).

Since NGF and BDNF share large regions of homology (approximately 50%), degenerate oligonucleotide primers corresponding to four of these regions were used in PCR reactions to amplify novel related sequences. A related neurotrophic factor called neurotrophin 3 (NT-3) was cloned (Maisonpierre et al., (1990) *Science*, 247: 1446–1451). NT-3 is found both centrally and peripherally and is capable of promoting survival of sensory and sympathetic neurons, including dorsal root ganglia (DRG) explants.

The three neurotrophins described above have different neuronal specificities. All three neurotrophins induced neurite outgrowth from DRG explants. NGF induces neurite outgrowth from sympathetic ganglia (SG) but not nodose ganglion (NG), whereas BDNF induces neurite outgrowth from NG but not SG. NT-3 promotes neurite outgrowth from NG and to a lesser extent from SG, suggesting a broader specificity than either NGF or BDNF (Lindsay et al., (1991) *Restor. Neurol. Neurosci.*, 2: 211–220).

Ciliary Neurotrophic Factor (CNTF; Lin et al., (1989) *Science*, 246: 1023) promotes survival of chicken embryo ciliary ganglia in vitro and was also found to support survival of cultured sympathetic, sensory and spinal motor neurons (Ip et al., (1991) *J. Physiol., Paris*, 85: 123–130). Local administration of this protein to the lesion site of newborn rats has been shown to prevent the degeneration of the corresponding motor neurons. CNTF also rescued motor neurons from developmental cell death (Henderson et al., (1993) *Restor. Neurol. Neurosci.*, 5: 15–28). CNTF contains a structural element called an AB loop, beginning at residue 43, which is believed to be important in binding to a C-terminal domain in CNTF, thus leading to functional activation of the cytokine (Bazan, (1991) *Neuron*, 7: 197–208). CNTF, as well as other neuropoietic cytokines, shares sequence/structure motifs with hematopoietic cytokines including interleukin-6 and granulocyte colony stimulating factor. A prominent sequence motif in the C-terminal ends of these cytokines is predicted to adopt a precise tertiary structure that may interact with the cytokine receptor (Bazan, ibid.).

Current models of cytokine-receptor binding (Sprang and Bazan, (1993) *Curr. Opin. Struct. Biol.*, 3:816) have highlighted the evolutionary conservation of a specific packing geometry between the A and D helices of the cytokine protein bundle core that form a major part of the receptor complex. This structure is common to most cytokines. The AB loop and helix D, proposed to be required for binding, are separated by a large stretch of amino acids in all cytokines (more than 50 amino acids). This implies that small peptides of approximately 20 amino acids would be inactive as receptor ligands and would fail to elicit a cellular response.

BRIEF DESCRIPTION OF THE FIGURES

FIG. 1a is a graph illustrating the neurite outgrowth response of NS20Y neuroblastoma cells treated with recombinant prosaposin (prosap-r), prosaposin isolated from milk (prosap-m), saposin C, active 22-mer peptide derived from saposin C and iodine labeled 18-mer derived from saposin C over the 0.01–0.5 µg/ml range. The concentration of effector protein, in µg/ml, is shown on the x-axis and the percentage of cells with neurites is shown on the y-axis.

FIG. 2 shows a bar graph indicating choline acetyltransferase (ChAT) activity induced by various effectors. SKNMC neuroblastoma cells were grown in DMEM containing 0.5% fetal calf serum (FCS) for 48 hours in the presence of effectors (200 ng/ml) and ChAT activity was measured. The effectors are shown on the x-axis and the incorporation of label (cpm/mg protein/min) is shown on the y-axis.

FIG. 3B provides a sequence alignment of the active 22-mer human saposin C sequence (SEQ ID NO: 1) with the same sequence from four other species (SEQ ID NOS: 15 to 18). The consensus (completely conserved) residues are indicated below the sequence alignment as SEQ ID NO: 19. The sequence of human saposin A (SEQ ID NO: 20; which is inactive) in the same region is provided to illustrate the divergence between the sequence of three of the first four residues in the same hydrophilic region (18–29) in saposin A but conservation of the remaining residues.

SUMMARY OF THE INVENTION

Figure 1B:
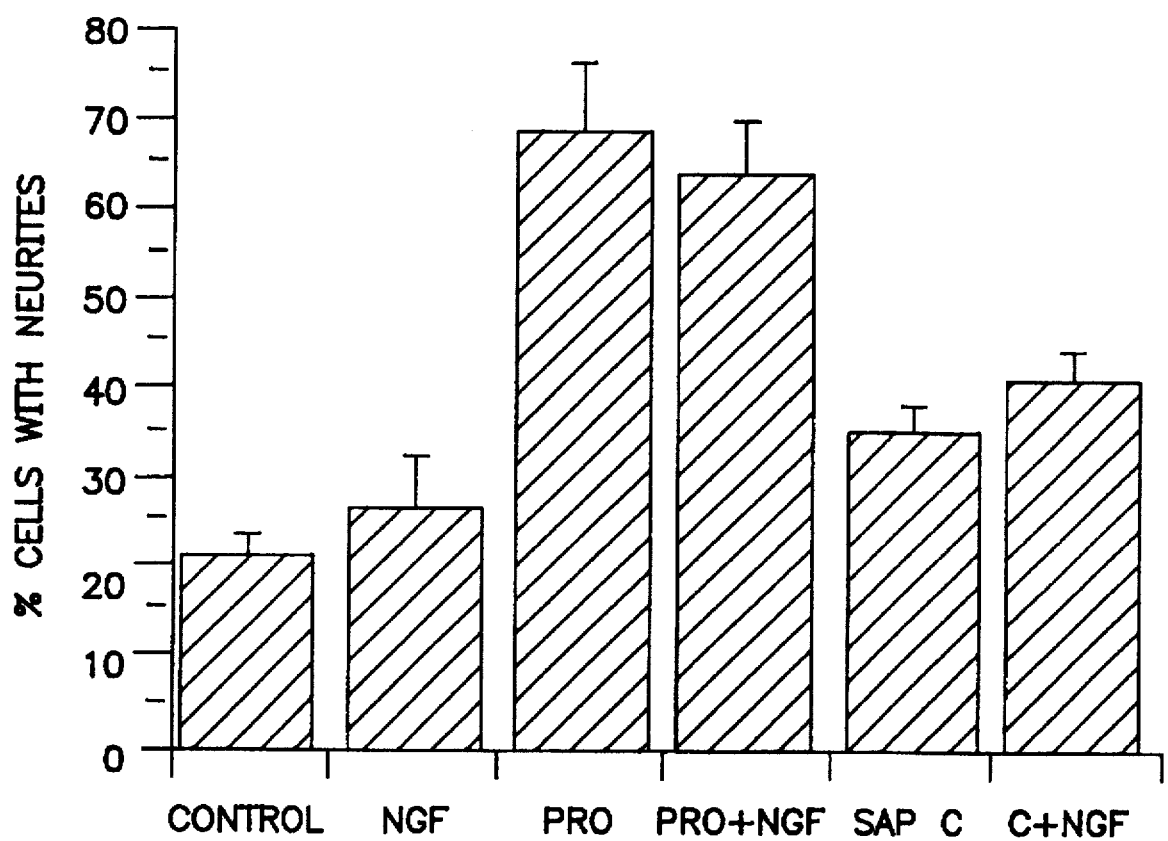
FIG. 1b is a bar graph showing the effect of 5 µg/ml NGF on neurite outgrowth in prosaposin and saposin C treated NS20Y cells. The y-axis indicates the percentage of cells with neurites.

One embodiment of the present invention is a method for stimulating neural cell outgrowth or increased myelination by contacting neuronal cells with a composition including prosaposin, saposin C or a peptide conforming to the consensus sequence described hereinbelow having the ability to promote increased neural outgrowth or increased myelination activity. Preferably, the prosaposin is native; most preferably, the prosaposin is recombinantly produced. The peptide may advantageously be saposin C, a peptide comprising amino acids 8–29 of saposin C, or the active neurotrophic fragment located within amino acids 8–29 of saposin C. Preferably, the neuronal cells are neuroblastoma cells and the peptide consists essentially of SEQ ID NOs: 2 or 7–14. These neuronal cells are preferably contacted in vitro and most preferably contacted in vivo. In another aspect of this preferred embodiment, the cells are from mouse cerebellar explants.

Another aspect of the present invention relates to a method for treatment of demyelination disorders in a mammal by identifying a mammal afflicted with the disorder, and administering to the mammal a pharmaceutically effective demyelination inhibiting amount of prosaposin, a neurotrophic fragment thereof, or a consensus peptide conforming to the rules described hereinbelow. Preferably, this fragment is saposin C and the demyelination disorder is either multiple sclerosis, acute disseminated leukoencephalitis, progressive multifocal leukoencephalitis or adrenal leukodystrophy. Advantageously, the method of administration is either intramuscular, intradermal, subcutaneous, intracranial, intracerebrospinal or topical in a biologically compatible carrier. The prosaposin or fragment thereof may be advantageously enclosed in a liposome-like (lamellar) structure.

The invention further comprises a method for halting or slowing the progress of neural or myelin degeneration in neural tissue, by contacting neuronal tissue susceptible to such degradation with prosaposin or an active degradation-inhibiting fragment thereof. Preferably, the fragment is saposin C and the tissue is in vitro; most preferably, the tissue is in vivo.

Another aspect of the present invention is a method for the treatment of neuronal degenerative diseases of the central or peripheral nervous system, by administering to a mammal suffering from such a disease an amount of a prosaposin fragment effective to retard or halt neuronal degeneration. Preferably, this fragment includes the neurotrophic activity of the peptide of SEQ ID NO: 1 and is administered intravenously, intramuscularly, intradermally, subcutaneously, intracranially, intracerebrospinally, topically or orally. Advantageously, the disease is a disease of the central nervous system and the fragment is selected to cross the blood brain barrier. In another aspect of this preferred embodiment, the disease is Alzheimer's disease, Parkinson's disease, stroke, post-polio syndrome or amyotrophic lateral sclerosis Further, the invention includes a method for retarding the progress of retinal neuropathy in a patient by administering to the patient an effective amount of prosaposin or a neurotrophic fragment thereof. Preferably, this retinal neuropathy is macular degeneration, the patient is a human over the age of 65, and the administration is either topical, intravenous, intraocular or oral.

Another aspect of the present invention is a pharmaceutical composition comprising prosaposin or a neurotrophic fragment thereof in unit dosage form.

Still another aspect of the present invention is a pharmaceutical composition comprising prosaposin or a neurotrophic fragment thereof formulated with a controlled release material.

The invention also includes a neural prosaposin receptor protein in isolated or purified form. Preferably, this receptor protein is isolated from a P100 plasma membrane fraction by affinity purification using a neurite growth-inducing peptide contained within the saposin C sequence linked to a solid support, and has a molecular weight of approximately 60 kDa.

In accordance with another aspect of the invention, there is provided an active neurotrophic peptide having between about 15 and about 50 amino acids, and including the consensus sequence XNNYZ, wherein N is asparagine and X, Y and Z are amino acids naturally occurring in mammalian proteins, the consensus sequence comprising:

two adjacent or next-adjacent asparagine residues;

a leucine or isoleucine residue X three or four residues towards the N-terminus of said asparagine residues;

one or more charged amino acid residues Y, wherein Y is located two to eight residues towards the C-terminus of said asparagine residues; and one or more hydrophobic residues Z, wherein Z is located six to ten residues towards the C-terminus of said asparagine residues, and the peptide induces neuritogenesis in cells.

In another aspect of this preferred embodiment, the asparagine residues are separated by one amino acid. Preferably, the peptide is derived from a cytokine and promotes the same process as the cytokine from which it is derived. Advantageously, the cytokine is interleukin-1, interleukin-2, interleukin-3, leukocyte inhibitory factor, erythropoietin, interleukin-6 or oncostatin-M. Further, the peptide includes the activity of SEQ ID NOs: 2, 7, 8, 9, 10, 11, or 12, and comprises from about 15 to about 50 amino acids of the AB loop of CNTF, interleukin-6, interleukin-2, interleukin-3, interleukin-1$_r$, erythropoietin, or leukocyte inhibitory factor, respectively. In another aspect of this embodiment, the peptide includes the activity of SEQ ID NO: 13 or 14, and comprises from about 15 to about 50 amino acids from helix C of IL-1β or oncostatin-M, respectively.

Another embodiment of the invention is a method for stimulating neural cell outgrowth, comprising contacting neuronal cells with a composition comprising an active peptide having the consensus sequence described hereinabove. Preferably, the neuronal cells are neuroblastoma cells and the cells are contacted in vitro; most preferably, the cells are contacted in vivo.

DETAILED DESCRIPTION OF THE INVENTION

The identification of prosaposin itself as a neurotrophic factor which is present in the cell bodies of large populations of neurons including upper and lower motor neurons, and its ability to induce myelination in mouse cerebellar explants, represent significant new functions for this protein. Additionally, the use of prosaposin peptides to promote cell growth and differentiation has not been described. Moreover, the ability of small peptides (conforming to the consensus sequence described below) derived from neuropoietic and hematopoietic cytokines to act as cytokines themselves has not been demonstrated. Thus, it is an object of the present invention to provide prosaposin, its derivatives, and peptides derived from various neurotrophic and hematopoietic cytokines for use as therapeutic agents.

The present invention discloses a neurotrophic peptide consensus sequence found in a number of neurotrophic and hematopoietic cytokines which will stimulate both neurite outgrowth and mimic the activity of the molecule from which it was derived. This consensus sequence is found in prosaposin, saposin C, a peptide comprising amino acids 8–29 of saposin C, and a 20-mer peptide comprising amino acids 38–57 of CNTF, all of which exhibited neuritogenic activity. Since the active 22-mer of saposin C exhibited sequence similarity to the CNTF 20-mer as well as to peptides derived from a number of hematopoietic cytokines including interleukin (IL)-1, IL-2 and erythropoietin (EPO), these peptides will also be useful as cytokine analogs. In addition, prosaposin, saposin C and the saposin C peptide can be used to promote increased myelination.

Prosaposin, its derivatives, the 20-mer CNTF peptide and consensus peptides derived from other neurotrophins, cytokines and growth factors possess significant therapeutic applications in promoting functional recovery after toxic, traumatic, ischemic, degenerative and inherited lesions to the peripheral and central nervous system. Small peptides derived from cytokines will also have utility in mediating similar effects to the cytokines themselves. The use of these peptides will facilitate treatment of various disorders since they will be more stable and easier to synthesize than either the native or recombinant cytokines. In addition, prosaposin and its derivatives may be used to counteract the effects of demyelinating diseases.

Prosaposin and its derivatives are known to be present in many types of neurons, are water soluble (in contrast to glycosphingolipids) and are less immunogenic than ganglioside micelles since for therapy in humans the human sequence will be used which will not elicit an immune response.

The active 22-mer peptide derived from saposin C has the amino acid sequence set forth in SEQ ID NO:1 (CEFLVKEVTKLIDNNKTEKEIL). The 20-mer CNTF peptide has the amino acid sequence set forth in SEQ ID NO:2 (YVKHQGLNKNINLDSVDGVP). Human prosaposin has the amino acid sequence set forth in SEQ ID NO:3. Saposin C has the amino acid sequence set forth in SEQ ID NO:4. The human cDNA sequence for prosaposin is set forth in SEQ ID NO:5. An active 18-mer fragment derived from the active 22-mer fragment is set forth as SEQ ID NO: 6 (YKEVTKLIDNNKTEKEIL).

As will be discussed in more specific detail in the examples, prosaposin, saposin C, amino acids of saposin C that include at least amino acids 8–29 and the CNTF 20-mer peptide are active as neurotrophic factors. In addition, a peptide including at least amino acids 12–29 (with a tyrosine substituted for valine at position 12) is also an active neurotrophic factor. It was observed that amino acid residues 8–29 of the saposin C sequence exhibited sequence similarity to residues 44–57 of CNTF.

A sequence alignment of CNTF with twenty different cytokines and growth factors revealed sequence similarity to human (h) IL-6, IL-2, IL-3, IL-1 γ chain, erythropoietin (EPO), human leukocyte inhibitory factor (LIF), IL-1 β chain, oncostatin-M as well as saposin C (Table 2).

TABLE 2

| Cytokine | Peptide | Location | SEQ ID NO: |
|---|---|---|---|
| SapC | CEFLVKEVTKLIDNNKTEKEIL | — | 1 |
| hCNTF | YVKHQGLNKNINLDSVDGVP | AB loop | 2 |
| hIL-6 | EALAENNLNLPKMAG | AB loop | 7 |
| hIL-2 | LQMILNGINNYKNPKLT | AB loop | 8 |
| hIL-3 | ILMENNLRRPNL | AB loop | 9 |
| hIL-γ | FYLRNNQLVAGTL | AB loop | 10 |
| hEPO | AEHCSLNENITVPDTKU | AB loop | 11 |
| hLIF | YTAQGEPFPNNVELKLCAP | AB loop | 12 |
| hIL-1β | FNKIEINNKLEFESA | Helix C | 13 |
| hONC-M | RPNILGLRNNIYCMAQLL | Helix C | 14 |

The sequence alignments define a consensus sequence XNNYZ. This consensus sequence was first discovered based upon a comparison of the prosaposin 22-mer from different species, and with a similar sequence from saposin A which is inactive as a neurotrophic factor.

The most important features of this consensus sequence (proper stimulating sequence or PSS) include two asparagine (N) residues, either adjacent or separated by one amino acid, a leucine (L) or isoleucine (I) residue X 3–4 residues upstream (toward the N-terminus) of the two asparagine residues, one or more charged residues Y (aspartic acid (D), lysine (K), glutamic acid (E), or arginine (R)) 2–8 residues downstream (toward the C-terminus) of the two asparagine residues and one or more hydrophobic residues Z (alanine (A), L, I or valine (V)) 6–10 residues downstream of the two asparagine residues. The CNTF, IL-6, IL-2, IL-3 and IL1-γ sequences conform most rigidly to the PSS, while the EPO and LIF sequences lack a leucine or isoleucine at position -4. The IL-1β and ONC-M sequences are not in the AB loop. It is intended that any peptide conforming to the rules described above is within the scope of the present invention.

The peptides listed in the table above may be prepared by conventional automated peptide synthesis and screened for neurotrophic activity as described in Example 1 by one of ordinary skill in the art. Similar active peptides derived from prosaposin or saposin C, also within the scope of this invention, can also be similarly prepared and screened. In addition, cytokine-derived peptides may be assayed for the activity of their corresponding cytokine. This is described in Examples 11 and 12 for IL-6 and EPO, respectively. These peptides will promote the same cellular processes as will the corresponding full length protein. For example, the IL-6 peptide will exhibit antiinflammatory activity by inhibiting tumor necrosis factor (TNF) release from activated macrophages and the EPO peptide will stimulate differentiation of stem cells (erythrocyte colony forming cells) into red blood cells. Those peptides derived from cytokines with neurotrophic activity will also stimulate the outgrowth of neurites, and may promote myelination and prevent programmed cell death in neuronal tissues.

In addition, it appears that these peptides, having from about 15 to about 50 amino acids, have the same categories of activity as the sequences of SEQ ID NOs: 1 and 2, and can be used in generally the same manner and provided in generally the same forms as those molecules. Thus, the disclosures of the present invention related to prosaposin, saposin C, and neurotrophic fragments thereof should be extended to the peptides of SEQ ID NOs: 2 and 7–14. Moreover, those sequences are disclosed in Table 2 as being derived from either the AB loop or helix C of the respective cytokines. Peptides having from about 15 to about 50 amino acids derived from those portions of the native molecule that maintain the activity of the described peptides are also within the scope of the present invention. Measurement of activity of any peptide of interest can be accomplished as set forth in the Examples, or by using an established assay for the activity of the molecule from which the peptide is derived.

One aspect of the present invention is a method for facilitating outgrowth of neurites in differentiated or undifferentiated neural cells. This method requires administration of an effective, neurite-outgrowth facilitating amount of prosaposin, saposin C, the 18 or 22 amino acid fragment thereof, the CNTF 20-mer peptide, or any of the peptides corresponding to the rules described above to the cells in question. A typical minimum amount of prosaposin for the neurotrophic factor activity in cell growth medium is usually at least about $1.4 \times 10^{-11}$M, or about 10 ng/ml. This amount or more of saposin C, its active 18 or 22 amino acid fragments, the CNTF 20-mer or any of the other peptides of the present invention may also be used. Usually concentrations in the range of 0.1 µg/ml to about 10 µg/ml of any of these materials will be used. Effective amounts for any particular tissue can be determined in accordance with Example 1.

The neural or hematopoietic cells can be treated in vitro or ex vivo by directly administering the protein or peptide factors of the present invention to the cells. This can be done, for example, by culturing the cells in growth medium suitable for the particular cell type followed by addition of the factor to the medium.

When the cells to be treated are in vivo, typically in a vertebrate, preferably a mammal or a bird, the composition can be administered to the cells to be treated by one of several techniques. Most preferably, the composition can be injected directly into the blood in sufficient quantity to give the desired concentration of neurotrophic or hematopoietic cytokine-derived peptide, since an iodinated 18-mer peptide consisting of amino acids 12–29 of the 22-mer with a substitution of tyrosine for valine at amino acid 12 (M.W.= 2000) crosses the blood brain barrier and enters the central nervous system as described in Example 7 (see Banks et al., (1992) *Peptides*, 13: 1289–1294). The uptake by the brain was approximately 0.03%, which is in the midrange of values for peptides of that approximate size which will cross the blood brain barrier. Although this is the only neurotrophic factor so far described which will cross the blood brain barrier when administered intravenously, the intravenous administration of any of the peptides of the present invention is contemplated.

Direct intracranial injection or injection into the cerebrospinal fluid may also be used in sufficient quantities to give the desired local concentration of protein or peptide. In both cases, a pharmaceutically acceptable injectable carrier of well known type can be used. Such carriers include, for example, phosphate buffered saline (PBS). Alternatively, the composition can be administered to peripheral neural tissue by direct local injection or by systemic administration. Various conventional modes of administration are contemplated, including intravenous, intramuscular, intradermal, subcutaneous, intracranial, epidural, topical and oral administration.

The composition can be packaged and administered in unit dosage form such as an injectable composition or local preparation in a dosage amount equivalent to the daily dosage administered to a patient or as a controlled release composition. A septum sealed vial containing a daily dose of the active ingredient in either PBS or in lyophilized form is an example of a unit dosage.

Since the molecular weight of the active 22-mer is approximately 2600, and an iodinated 18-mer contained within this sequence will cross the blood brain barrier, then the 22-mer will also most likely cross and enter the central nervous system (Banks et al., (1992) *Peptides,* 13: 1289–1294). It is also contemplated that the CNTF 20-mer as well as peptides derived from other cytokines will also cross this barrier. Appropriate daily systemic dosages based on the body weight of the vertebrate are in the range of from about 10 to about 100 µg/kg, although dosages from about 0.1 to about 1000 µg/kg are also contemplated. Daily dosages of locally administered material will be about an order of magnitude less. Oral administration may be possible if the peptide is stable to gastrointestinal degradation and readily absorbed.

In one preferred embodiment of the invention, the protein or peptide factor is administered locally to the neural cells in vivo by implantation of the material. For example, polylactic acid, polygalactic acid, regenerated collagen, multilamellar liposomes and many other conventional depot formulations comprise bioerodible or biodegradable materials that can be formulated with biologically active compositions. These materials, when implanted, gradually break down and release the active material to the surrounding tissue. The use of bioerodible, biodegradable and other depot formulations is expressly contemplated in the present invention. Infusion pumps, matrix entrapment systems, and combination with transdermal delivery devices are also contemplated.

The protein and peptide factors of the present invention may also advantageously be enclosed in micelles or liposomes. Liposome encapsulation technology is well known. Liposomes may be targeted to specific tissue, such as neural tissue, through the use of receptors, ligands or antibodies capable of binding the targeted tissue. The preparation of these formulations is well known in the art (i.e., Radin and Metz, (1983) *Methods Enzymol.,* 98: 613–618).

There are currently no available pharmaceuticals able to promote full functional regeneration and restoration of structural integrity of neural systems. This is particularly true of the central nervous system. Regeneration of peripheral nerves through use of neurotrophic factors is a more immediately demonstrable goal. Such treatment is within the scope of this invention. Moreover, neurotrophic factors can be therapeutically useful in the treatment of neurodegenerative diseases associated with the degeneration of neural populations or specific areas of the brain. The principal cause of Parkinson's disease is the degeneration of dopaminergic neurons of the substantia nigra. Since antibodies against prosaposin immunohistochemically stain the dopaminergic neurons of the substantia nigra in human brain sections, prosaposin and its active fragments may be therapeutically useful in the treatment of Parkinson's disease. Since local administration of CNTF to the lesion site of newborn rats has been shown to prevent the degeneration of the corresponding motor neurons and CNTF can also rescue motor neurons from developmental cell death, the use of the CNTF peptide or any of the peptides of the present invention may also have therapeutic applications in neurodegenerative diseases.

It has long been believed that in order to reach neuronal populations in the brain, neurotrophic factors would have to be administered intracerebrally, since these proteins do not cross the blood-brain barrier. However, as previously mentioned, the active iodinated 18-mer will cross and the active 22-mer will most likely cross this barrier and would thus be administered intravenously. Other neuronal populations, such as motor neurons, would also be treated by intravenous injection, although direct injection into the cerebrospinal fluid is also envisioned as an alternate route.

Cells may be treated to facilitate myelin formation or to prevent demyelination in the manner described above, both in vitro, ex vivo and in vivo. There are several diseases that result in demyelination of nerve fibers including multiple sclerosis, acute disseminated leukoencephalitis, progressive multifocal leukoencephalitis, metachromatic leukodystrophy and adrenal leukodystrophy. These diseases can be treated, and the progression of the demyelination can be slowed or halted, by administration of the neurotrophic factors of the present invention to the cells affected by the disease. Although only prosaposin and its derivatives have been tested in the myelination assay (Example 2), it is contemplated that the 20-mer CNTF peptide would also promote increased myelination.

The compositions of the present invention can be used in vitro as research tools for studying the effects of cytokines, neurotrophic factors and myelin facilitating materials. However, more practically, they have an immediate use as laboratory reagents and components of cell growth media in order to better enable growth of cells in vitro.

The prosaposin used in the present invention may be obtained from various sources, and may be, for example, naturally occurring protein isolated from human milk or seminal plasma or recombinant human prosaposin purified from spent media of *Spodoptera frugiperda* (Sf9) cells infected with a baculovirus expression vector containing full-length cDNA for human prosaposin as described (Dewji et al., (1987) *Proc. Natl. Acad. Sci. USA,* 84: 8652–8656). O'Brien et al., (1988) *Science,* 241: 1098–1101); Hiraiwa et al., (1993) *Arch. Biochem. Biophys.,* 304, 110–116). Saposin C is isolated in pure form from spleens of patients with Gaucher disease, a lysosomal storage disorder (Morimoto et al., (1990) *Proc. Natl. Acad. Sci. USA,* 87: 3493–3497). Saposin C (80 amino acids) can also be chemically synthesized and refolded (Weiler et al., (1993) *J. Mol. Neurosci.,* 4: 161–172).

The peptides corresponding to sequences within saposin C, and the other peptides described hereinabove, may be synthesized using an automated solid-phase protocol on an Applied Biosystems Model 430 peptide synthesizer. After synthesis, peptides are desalted on a Sephadex G-75 column prior to use.

EXAMPLE 1

Effect of prosaposin, saposins, CNTF and NGF on NS20Y neurite outgrowth and choline acetyltransferase activity NS20Y neuroblastoma cells were grown in Dulbecco's Modified Eagle Medium (DMEM) containing 10% fetal calf serum (FCS) and 1 mM sodium pyruvate. Cells were removed with trypsin and plated in 30 mm petri dishes onto glass coverslips. After 20–24 hours the medium was replaced with DMEM containing 0.5% fetal calf serum plus effector proteins. Cells were cultured for another 24 hours, washed with phosphate buffered saline (PBS) and fixed with Bouin's solution (saturated aqueous picric acid/formalin/ acetic acid 15:5:1) for 30 minutes. Fixative was removed with PBS and neurite outgrowth was scored under a phase contrast microscope. Cells exhibiting one or more clearly defined neurites equal to or longer than one cell diameter were scored as positive. At least 200 cells were scored in different portions of each dish to determine the percentage of neurite bearing cells and assays were performed in duplicate.

A dose-response curve (FIG. 1a) demonstrated that prosaposin promoted reversible neurite outgrowth in NS20Y neuroblastoma cells. The lowest concentration for activity was $1.4 \times 10^{-11}$M (10 ng/ml) which is in the effective concentration range of other neurotrophins. When prosaposin was removed, retraction of neurite outgrowth was complete at 36 hours, demonstrating that its continual presence is necessary in order to maintain neurite outgrowth. In addition, saposin C was the sole fragment of prosaposin found to possess neurotogenic activity, as did the 22-mer and iodinated 18-mer peptides derived from the saposin C sequence.

Since nerve growth factor (NGF) acts on a variety of cell types, we wanted to determine whether it was involved in prosaposin-mediated outgrowth in neuroblastoma cells. NGF by itself had no effect on neurite outgrowth in NS20Y cells and did not augment the prosaposin response (FIG. 1b). When 5'-methyladenosine (MeSAdo), which specifically inhibits NGF-induced neuritogenesis in PC12M pheochromocytoma cells was added, MeSAdo did not inhibit prosaposin-induced NS20Y neurite outgrowth. Additionally, prosaposin failed to stimulate neurite outgrowth from NGF-responsive PC12M cells at high concentrations (2 mg/ml). Since NS20Y cells are not NGF responsive, this indicates that the NGF response and the prosaposin response are different.

Figure 1C:
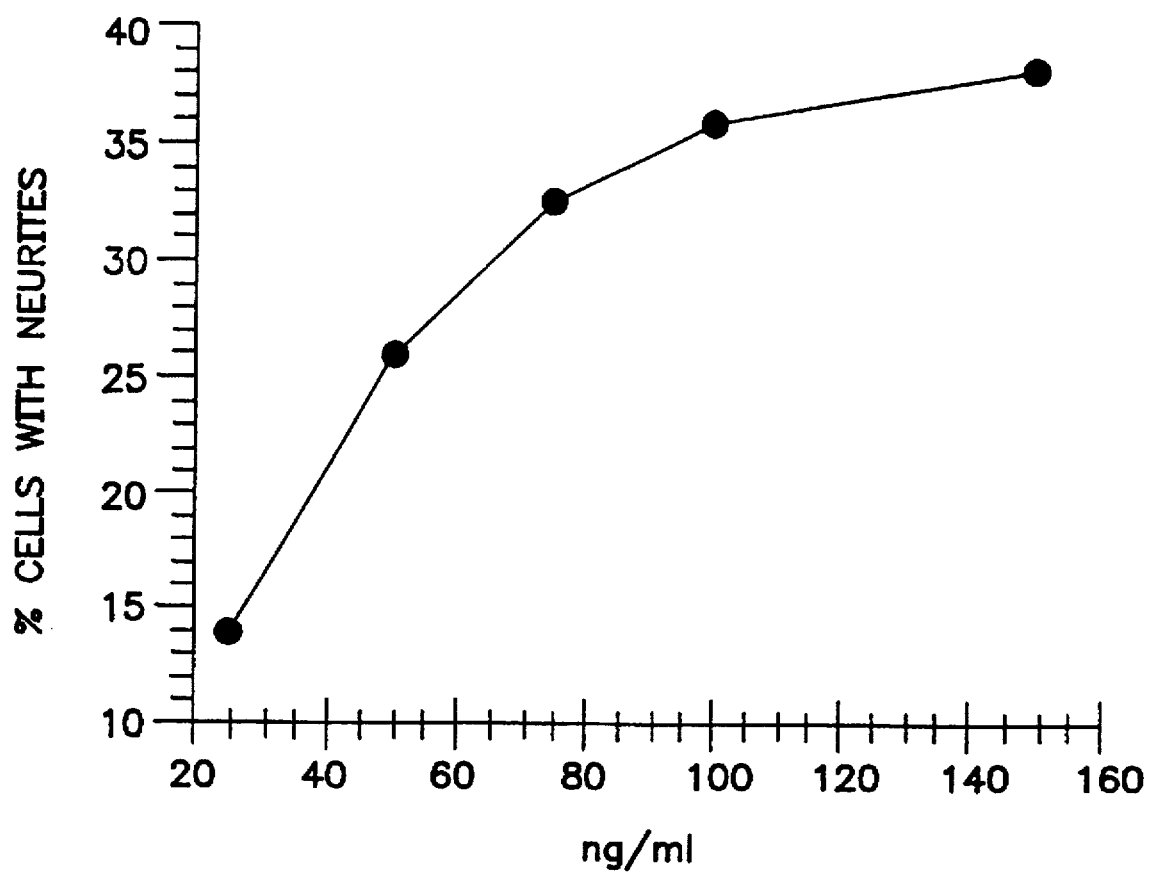
FIG. 1c is a graph showing the effect of a 20 residue peptide derived from CNTF called peptide 9 (SEQ ID NO: 2) on the neurite outgrowth response of NS20Y neuroblastoma cells. The concentration of peptide is shown on the x-axis and the percentage of cells with neurites is shown on the y-axis.

The CNTF-derived 20-mer peptide (SEQ ID NO: 2), peptide 9, also stimulated neurite outgrowth in NS20Y neuroblastoma cells (FIG. 1c). In fact, peptide 9 stimulated neurite outgrowth at concentrations about 10-fold higher than CNTF on a molar basis.

Figure 1D:
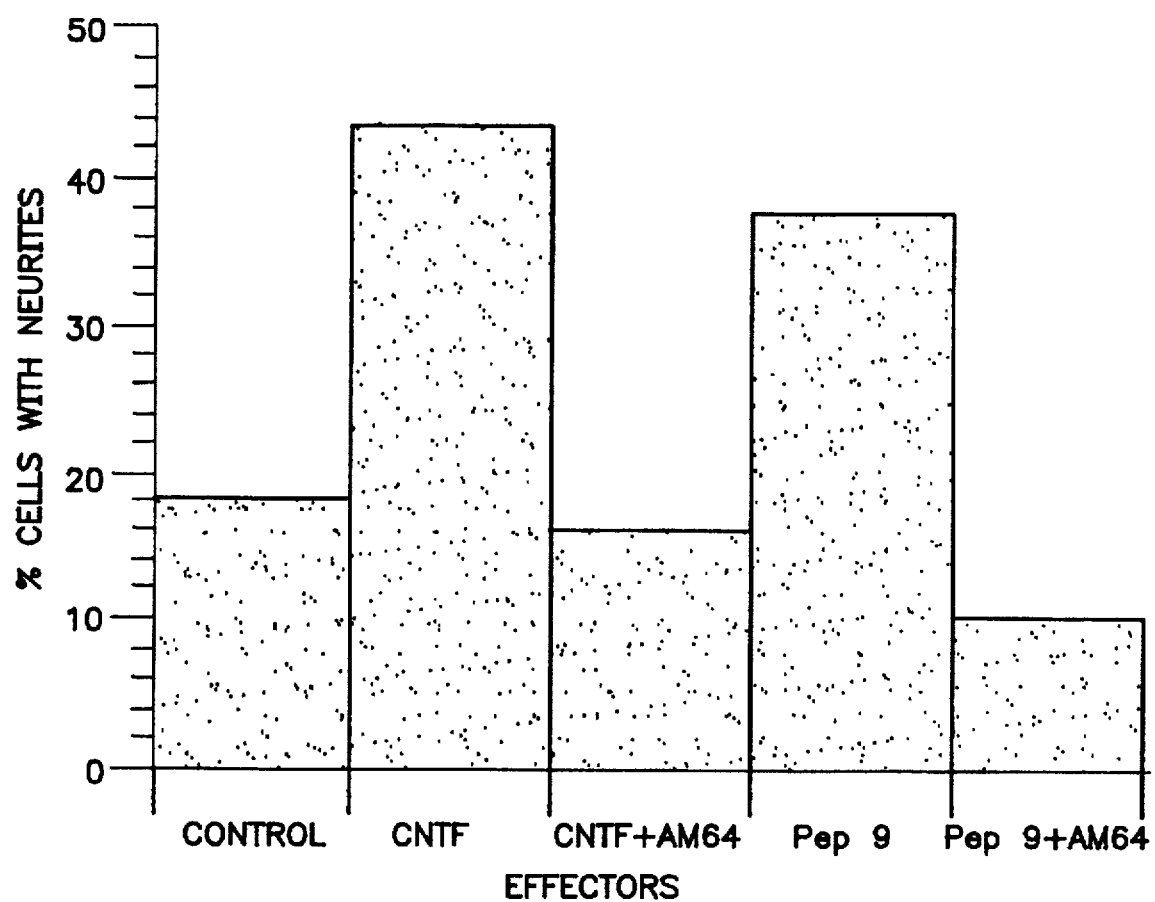
FIG. 1d is a bar graph showing the effect of CNTF and Peptide 9, either alone or in the presence of antibody AM64, a monoclonal antibody against glycoprotein 130 (gp130), on neurite outgrowth in NS20Y neuroblastoma cells. CNTF and Peptide 9 were added to the media at 100 ng/ml and 20 ng/ml, respectively. The effectors are shown on the x-axis and the percentage of cells with neurite outgrowths is shown on the y-axis.

The stimulation of neurite outgrowth by peptide 9 and CNTF was completely blocked by a monoclonal antibody AM64 against a cell surface glycoprotein, gp 130 (FIG. 1d). This protein is a β-receptor component of the CNTF receptor complex and is required for CNTF-induced signal transduction.

The ability of prosaposin, its derivatives, CNTF and the CNTF 20-mer to stimulate choline acetyltransferase (ChAT) was then determined. ChAT is an enzyme catalyzing the synthesis of the neurotransmitter acetylcholine and increased levels of the enzyme indicate increased levels of neuronal differentiation.

SKNMC neuroblastoma cells (American Type Culture Collection, Rockville, Md.; ATCC HTB 10) were cultured for 48 hours in the presence of 200 ng/ml of either saposin C, the saposin C 22-mer, prosaposin, CNTF, the CNTF peptide, peptide 9 or saposin A. ChAT activity was then measured by the transfer of [$^{14}$C]-acetyl groups from acetyl-CoA to choline (Fonnun, (1975) *J. Neurochem.*, 24:407–409). The results indicated that all of the peptides with the exception of saposin A stimulated ChAT activity.

Figure 3A:
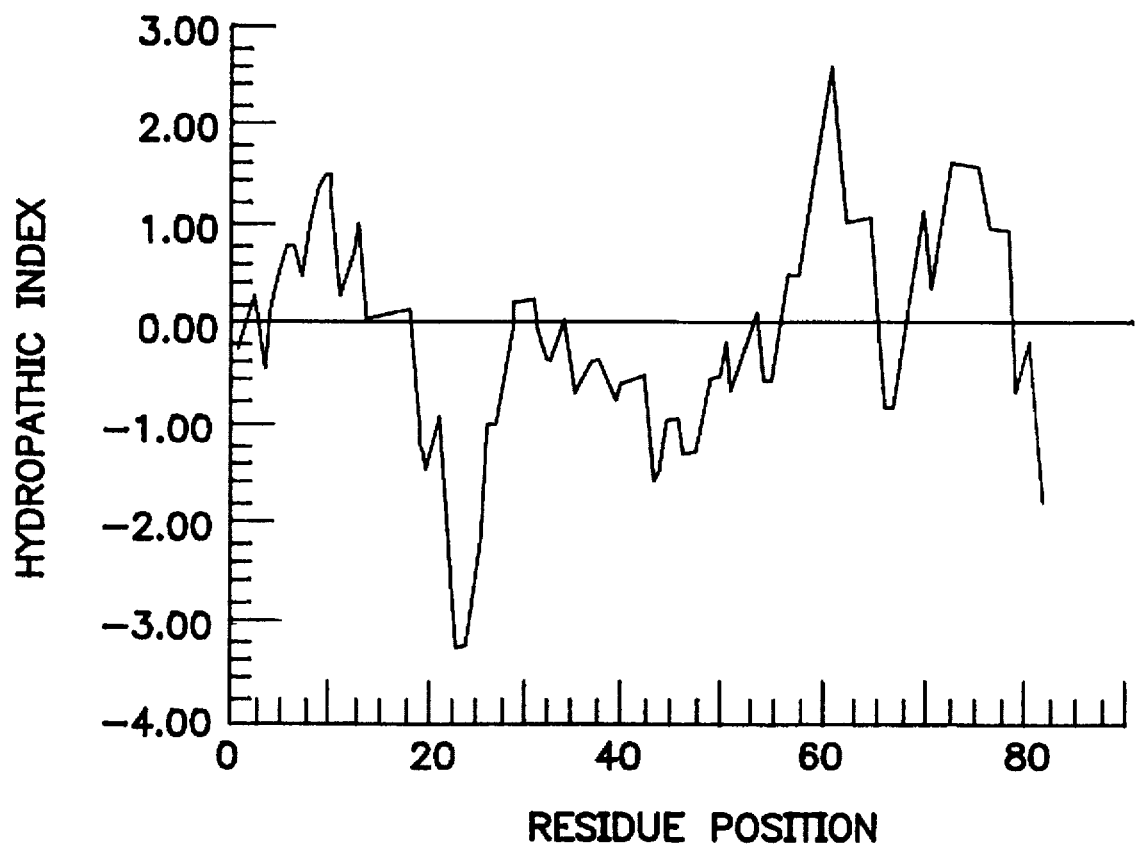
FIG. 3a shows a hydropathy plot of the human saposin C sequence. The amino acid residue position is shown on the x-axis and the hydropathic index is shown on the y-axis.

A set of synthetic peptides from different regions of saposin C was utilized to further define the active sequence. An amino terminal peptide (1–40) was active and a carboxy terminal peptide (41–82) was inactive. Testing of four more peptides (Table 3) further narrowed the active sequence to a region between residues 8–29, the most hydrophilic region in the saposin C domain (FIG. 3a) which also contains the single glycosylation site (Asn 22). Higher concentrations of the active 22-mer (residues 8–29) were required for activity but the extent of neurite outgrowth was greater than with prosaposin or saposin C (FIG. 1a). The sequence between residues 18 and 29 is highly conserved (FIG. 3b). Interestingly, human saposin A is nearly identical to saposin C in this region except for the first four residues, indicating that the active sequence requires the presence of leucine 18 and asparagines at residues 21 and 22 or both.

TABLE 3

Neurite outgrowth response of NS20Y cells treated with human saposin C, saposin A and synthetic peptides from the human saposin C domain at 5 µg/ml. The dose response curve for peptide 8–29 (active 22 mer) is given in FIG. 1a.

| Peptide Added (5 µg/ml) | % Neurites after 24 hours |
|---|---|
| Saposin C | 40% |
| 1–40 | 42% |
| 41–82 | 17% |
| 1–27 | 46% |
| 13–34 | 50% |
| 21–48 | 18% |
| 8–29 | 56% |
| Saposin A | 20% |
| None | 18% |

To test whether gangliosides were involved in the response, a prosaposin-ganglioside GM1 complex (4:1) was generated by a method well known in the art. When tested in the neurite outgrowth assay, the complex had negligible activity. The same result was obtained with a ganglioside GM3-saposin C complex. This indicated that the neurotogenic effect was not the result of ganglioside transport, but was instead due to the prosaposin and saposin C, respectively.

In order to determine whether prosaposin or its fragments would have an effect on neurite outgrowth in nontransformed cells, newborn mouse cerebellar explants were used as described in the following example:

EXAMPLE 2

Effect of prosaposin and its active fragments on neurite outgrowth in mouse cerebellar explants Newborn mouse cerebellar explants were prepared according to Satomi (*Zool. Sci.* 9, 127–137 (1992)). Neurite outgrowth and myelination were observed over 22 days in culture, during the period when the newborn mouse cerebellum normally undergoes neuronal differentiation and myelination begins. Prosaposin (5 µg/ml) and saposins A, B and C (10 µg/ml) were added on the second day after preparation of the explants (three control and three treated explants) and outgrowth of neurites and myelination were assessed under a bright field microscope with a video camera. On the eighth day cultures containing prosaposin and saposin C became thinner and more spread out than control cultures. On day 15, the prosaposin and saposin C treated cultures contained many cells with long projections at the periphery of the explant which were less prominent in controls or those treated with saposins A or B. Saposin C treated cultures contained twice as many myelinated axons in the subcortical white matter at 22 days as controls or those treated with saposins A or B. Both the number of myelinated fibers observed visually per optical field and the activity of the myelin marker enzyme CNP were twice the control value. These results demonstrate that the neurotrophic effect of prosaposin and saposin C also occurs in differentiating cerebellum ex vivo. These results further demonstrate the ability of prosaposin and saposin C to induce increased myelination in differentiating cerebellum ex vivo. It is also contemplated that any peptide sequence conforming the to rules described hereinabove will be useful in promoting increased myelination in vivo.

Since prosaposin appears to be active at the plasma membrane it should be present in the plasma membranes of responsive cells as shown in the following example:

EXAMPLE 3

Western blots of prosaposin and saposin C from NS20Y cells

NS20Y cells were grown to confluence in 75 cm flasks in the presence of growth medium. Cells were harvested by scraping and surface membranes were isolated by the zinc ion method of Warren and Glick (1969) using discontinuous gradients of 50, 48, 45, 43, 40 and 35% sucrose; surface membranes localize in the 40 and 43% sucrose fraction. These fractions, as well as the infranatant and supernatant fractions bounding them, were electrophoresed on 10% SDS polyacrylamide gels along with the whole cell extracts, transferred to nitrocellulose filters, and probed with a monoclonal antibody to saposin C by methods well known in the art.

Examination of Western blots revealed that prosaposin, migrating as a 68 kDa band on SDS polyacrylamide gels, was localized to surface membrane fractions from both NS20Y and Neuro 2A cells. Mature saposin C and intermediate molecular weight saposin derivatives were minor components of the membrane fractions but were abundant in the whole cell extract. This demonstrates that prosaposin is located in the plasma membrane of responsive cells.

In order to localize prosaposin histochemically, neuroblastoma cell lines were immunostained with a prosaposin-specific antibody (JP-1) as illustrated in the following example:

EXAMPLE 4

Immunohistochemical localization of prosaposin

Cells were grown on glass cover slips, washed three times with PBS and fixed with Bouin's solution for one hour at room temperature. Bouin's solution was then rinsed out with 5 washes of PBS and slips were incubated in 30% goat serum, 0.5% Tween 20 in PBS to block nonspecific binding and, after rinsing, were incubated in a 1:100 dilution of IgG purified rabbit JP-1 at 4° C. overnight. After rinsing with PBS containing 0.1% Triton X-100, the preparations were incubated with either peroxidase conjugated goat anti-rabbit IgG (Bio-Rad, 1:2000) or FITC-conjugated goat anti-rabbit IgG (Cappel, 1:2000). After rinsing, peroxidase immunostaining was detected using the imidazole-diaminobenzidine-$H_2O_2$ reaction. Fluorescence immunostaining was detected under a fluorescence microscope using Nofade as a quenching deterrent. Preimmune rabbit IgG (1:100) was used as a control for nonspecific binding. Immunostaining of extended neurites, plasma membranes and growth cones were observed.

A similar methodology was used to immunostain postmortem human brain sections to detect reactive cell types. In frontal cortex, intense staining of the perikarya of large and medium sized Golgi type 1 neurons was observed. The surface of neuronal perikarya and the proximal segment of axons at the hillock region were also strongly stained as were some extended axons. In the cerebellum strong staining of Purkinje and stellate cells was observed, as well as large neurons in the cerebellar nuclei (dentate, emboliform and globose nuclei). Cerebellar granular cells were moderately stained. In the mesencephalon, moderate staining was observed in dopaminergic neurons of the substantia nigra. Large neurons in the red nucleus, neurons in the oculomotor nucleus, the amygdaloid nucleus and ependymal cells lining the lateral ventricle were also moderately stained. In the hippocampus, pyramidal cells and granule cells of the dentate gyrus were strongly stained. In the spinal cord alpha motor neurons were intensely stained. This survey indicated that prosaposin was localized to populations of large neurons including upper and lower motor neurons.

Since all neurotrophins identified thus far exert their effects by binding to a cell surface receptor and initiating a kinase cascade, phosphorylation assays were performed in NS20Y cells treated with prosaposin or its fragments as described in the following example:

EXAMPLE 5

Incorporation of 32P into NS20Y proteins after treatment with prosaposin or its active fragments NS20Y cells were incubated in phosphate-free Hanks' balanced salt solution containing 2.5 µg/ml actinomycin D and 80–100 µCi/ml carrier-free [$^{32}$P]-orthophosphate (New England Nuclear) and effector proteins (0.5–1.0 µg/ml) and incubated for 10–15 minutes at room temperature. Cells were solubilized in SDS-PAGE sample buffer, analyzed by SDS-PAGE and autoradiographed.

Prosaposin, saposin C and SEQ ID NO: 1 were found to stimulate phosphorylation of proteins of 148, 100, 80, 68, 50, 38 and 34 kDa to a greater extent than controls or cells treated with similar concentrations of saposins A, B or D. This 148 kDa protein may be phospholipase C-γ, a protein known to be involved in phospholipid metabolism and which is phosphorylated on tyrosine residues in response to a number of growth factors. Densitometric analysis indicated a 3–5 fold stimulation of phosphorylation after 10 minutes. Treatment of gels with alkali revealed that the prominent phosphorylated proteins were alkali-resistant, indicating that they contain phosphotyrosine and/or phosphothreonine (located next to proline) residues. These results indicate that prosaposin and its active fragments bind to a cell surface receptor and activate a kinase cascade, similar to other neurotrophins and growth factors.

Since prosaposin-ganglioside GM1 or saposin C-ganglioside GM3 complexes inhibit neuritogenesis, while prosaposin or saposin C alone promote this process, this indicates that gangliosides may abolish neurotogenic activity by masking a receptor binding site on the neurotrophin. In addition, since prosaposin and its active fragments induce tyrosine phosphorylation of cytoplasmic proteins in responsive cells, most likely by activation of a tyrosine kinase(s)

similar to cytokines and growth factors, this provides further evidence that a cell surface receptor is involved.

A 20 kDa protein has been identified as the putative receptor for prosaposin as described in the following example:

EXAMPLE 6

Isolation of the prosaposin receptor

The putative prosaposin receptor protein was isolated from whole rat brain, rat cerebellum and mouse neuroblastoma cells using the plasma membrane P-100 fraction. Briefly, cells or tissues were solubilized and centrifuged at 14,000 rpm to remove debris. The supernatant was centrifuged at 40,000 rpm for 1 hour at 4° C. The pellet, enriched in plasma membrane, was solubilized in RIPA buffer (10 mM MOPS, pH 7.5, 0.3M sucrose, 5 mM EDTA, 1% Trasylol, 10 µM leupeptin and 10 µM antipain). This P-100 fraction was applied to an affinity column containing the bound, active 22-mer fragment of saposin C. The column was washed with 0.05M NaCl to elute loosely-bound proteins followed by 0.25M NaCl which eluted the putative 60 kDa prosaposin receptor. In addition, it was determined that the 60 kDa protein could be eluted using a 100 fold excess of unbound peptide thus demonstrating specific elution. The 60 kDa protein was approximately 90% pure as judged by SDS-PAGE. The protein was purified to homogeneity using HPLC and eluted at 50% acetonitrile in an acetonitrile/water gradient on a Vydac C4 column. After treatment with the cross-linking reagent disuccinimidyl suberate (DSS; Pierce, Rockford, Ill.), the 60 kDa protein bound irreversibly to $^{125}$I labeled saposin C as evidenced by the 72 kDa molecular weight of the complex (60 kDa+12 kDa).

EXAMPLE 7

In vivo peptide uptake by the central nervous system

An 18-mer peptide consisting of amino acids 12–29 of saposin C with a tyrosine substituted for valine at position 12 was chemically synthesized on an Applied Biosystems Model 430 peptide synthesizer. The peptide was then radio-iodinated by the lactoperoxidase method and 20×10$^6$ cpm were injected into the auricles of rats. The animals were sacrificed after one hour and 24 hours and the hearts were perfused with isotonic saline in order to remove the blood from the brain. The brain was then counted in a gamma counter in order to determine the percentage of peptide uptake. In addition, in the 24 hour experiment the brain was homogenized and separated into a capillary rich fraction (pellet) and a parenchymal brain fraction (supernatant) after dextran centrifugation (Triguero et al., (1990) *J. Neurochem.*, 54: 1882–1888). This method allows for the discrimination between radiolabeled peptide within blood vessels and that within the brain. In the 24 hour experiment, 0.017% of the injected peptide was detected in whole brian; 75% of the label was in the parenchymal fraction and 25% was in the capillary fraction. At 1 hour 0.03% of the injected dose was present in whole brain.

EXAMPLE 8

Use of prosaposin and its active fragments in treating traumatic ischemic lesions to the CNS in vivo Rats with traumatic lesions to the spinal cord receive direct or intravenous administration of prosaposin, its active fragments or a peptide conforming to the consensus sequence described hereinabove in the 10 ng-10 mg/ml range in a sterile saline solution or in a depot form to enable slow release. The same number of animals receive only saline. After surgical partial transection of the spinal cord or a crush injury, prosaposin or a neurotrophic fragment thereof is directly injected into the lesion site using the same dose range (control animals receive saline injections) and improvement is assessed by gain of motor neuron function (i.e., increased limb movement). The treatments continue until no further improvement occurs. Since prosaposin and its active fragments are very water-soluble, no special delivery system for the preparation is required. Injection of the peptides is preferred since there is less chance of degradation and diffusion will be greater. Additionally, these fragments can be chemically synthesized in large quantities.

EXAMPLE 9

Use of prosaposin and its active fragments in treating demyelination disorders

Patients diagnosed with early stage MS (or other demyelination disorder) are given the active 18 or 22-mer fragment of saposin C or any of the cytokine-derived consensus peptides (in saline) by direct intravenous injection or injection into the cerebrospinal fluid using the same dose range as in Example 7. Control patients receive only saline. The treatment is administered weekly or monthly and any improvement is assessed by increased muscle strength, musculoskeletal coordination, and assessing myelination by magnetic resonance imaging.

EXAMPLE 10

Use of prosaposin or its active fragments in treating retinal neuropathy

Retinal neuropathy, an ocular neurodegenerative disorder leading to loss of vision in the elderly, is believed to be a disorder treatable by prosaposin or its active fragments. Prosaposin, its active neurotrophic fragments, or one of the consensus peptides described hereinabove are administered either topically, systemically or intraocularly in an amount sufficient to produce a local concentration of neurotrophin of about 10 ng/ml to about 10 µg/ml. The administration is continued weekly until visual loss is slowed or no further increase in vision is noticed.

EXAMPLE 11

Inhibition of TNF release by IL-6-derived peptide

The IL-6-derived peptide described in Table 2 (SEQ ID NO: 9), a mutant PSS peptide containing an aspartate residue in place of the upstream asparagine, or a scrambled control peptide is added to macrophages in culture. An untreated culture acts as a control. The macrophages are activated by the addition of bacterial lipopolysaccharide (LPS; Sigma, St. Louis, Mo.) resulting in release of TNF into the culture medium which initiates an inflammatory cascade. IL-6 is known to inhibit the LPS-induced release of TNF (Aderka et al., (1989) *J. Immunol.*, 143:3517–3523). In cultures treated with the IL-6 peptide prior to LPS stimulation, the amount of TNF released will be significantly reduced compared to cultures not given the peptide. The degree of inhibition of TNF release will be similar for both IL-6 and the IL-6-derived peptide, while the mutant and scrambled peptides will not inhibit TNF release.

EXAMPLE 12

Stimulation of Erythropoiesis by the EPO-derived peptide

Spleen-derived erythroid progenitor cells from phenylhydrazine-treated mice are cultured using well known techniques. Cells are then treated with either recombinant human EPO, the EPO-derived peptide or a mutant EPO peptide containing an aspartate residue in place of the upstream asparagine. Cell proliferation is measured by the incorporation of [$^3$H]-thymidine into DNA following three days in culture (Krystal, (1983) *Exp. Hematol.*, 11:649–654). The cells are then washed, lysed and incorporated thymidine determined by scintillation counting. The EPO and EPO-derived peptides will significantly stimulate [$^3$H]-thymidine incorporation, whereas the mutant peptide will not stimulate incorporation above control levels.

---

What is claimed is:

1. A peptide consisting of the sequence YVKHQGLNKNINLDSVDGVP (SEQ ID NO: 2).

2. A peptide consisting of the sequence EALAENNLNLPKMAG (SEQ ID NO: 7).

3. A peptide consisting of the sequence LQMILNGINNYKNPKLT (SEQ ID NO: 8).

4. A peptide consisting of the sequence ILMENNLRRPNL (SEQ ID NO: 9).

5. A peptide consisting of the sequence FYLRNNQLVAGTL (SEQ ID NO: 10).

6. A peptide consisting of the sequence AEHCSLNENITVPDTKV (SEQ ID NO: 11).

7. A peptide consisting of the sequence YTAQGEPFPNNVEKLCAP (SEQ ID NO: 12).

8. A peptide consisting of the sequence FNKIEINNTKLEFESA (SEQ ID NO: 13).

9. A peptide consisting of the sequence RPNILGLRNNTYCMAQLL (SEQ ID NO: 14).

* * * * *